US011801297B2

(12) United States Patent
Langedijk et al.

(10) Patent No.: US 11,801,297 B2
(45) Date of Patent: *Oct. 31, 2023

(54) VACCINE AGAINST RSV

(71) Applicant: Janssen Vaccines & Prevention B.V., Leiden (NL)

(72) Inventors: Johannes Petrus Maria Langedijk, Amsterdam (NL); Janneke M. Verhagen, Amsterdam (NL)

(73) Assignee: Janssen Vaccines & Prevention B.V., Leiden (NL)

(*) Notice: Subject to any disclaimer, the term of this patent is extended or adjusted under 35 U.S.C. 154(b) by 0 days.

This patent is subject to a terminal disclaimer.

(21) Appl. No.: 17/664,290

(22) Filed: May 20, 2022

(65) Prior Publication Data
US 2022/0288186 A1 Sep. 15, 2022

Related U.S. Application Data

(63) Continuation of application No. 16/946,485, filed on Jun. 24, 2020, now Pat. No. 11,338,031, which is a continuation of application No. 16/091,257, filed as application No. PCT/EP2017/057957 on Apr. 4, 2017, now Pat. No. 10,729,757.

(30) Foreign Application Priority Data

Apr. 5, 2016 (EP) .................................. 16163807

(51) Int. Cl.
*A61K 39/12* (2006.01)
*A61K 39/00* (2006.01)

(52) U.S. Cl.
CPC ...... *A61K 39/12* (2013.01); *A61K 2039/5256* (2013.01); *A61K 2039/53* (2013.01); *C12N 2710/10041* (2013.01); *C12N 2760/18522* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

| 4,235,877 | A | 11/1980 | Fullerton |
| 4,372,945 | A | 2/1983 | Likhite |
| 4,474,757 | A | 10/1984 | Amon et al. |
| 5,057,540 | A | 10/1991 | Kensil et al. |
| 5,122,458 | A | 6/1992 | Post et al. |
| 5,385,839 | A | 1/1995 | Stinski |
| 5,559,099 | A | 9/1996 | Wickham et al. |
| 5,837,511 | A | 11/1998 | Falck-Pedersen et al. |
| 5,837,520 | A | 11/1998 | Shabram et al. |
| 5,846,782 | A | 12/1998 | Wickham et al. |
| 5,851,806 | A | 12/1998 | Kovesdi |
| 5,891,690 | A | 4/1999 | Massie |
| 5,965,541 | A | 10/1999 | Wickham et al. |
| 5,981,225 | A | 11/1999 | Kochanek et al. |
| 5,994,106 | A | 11/1999 | Kovesdi |
| 5,994,128 | A | 11/1999 | Fallaux et al. |
| 6,020,191 | A | 2/2000 | Scaria et al. |
| 6,040,174 | A | 3/2000 | Imler et al. |
| 6,083,716 | A | 7/2000 | Wilson et al. |
| 6,113,913 | A | 9/2000 | Brough et al. |
| 6,225,289 | B1 | 5/2001 | Kovesdi |
| 6,261,823 | B1 | 7/2001 | Tang |
| 6,485,958 | B2 | 11/2002 | Blanche |
| 7,270,811 | B2 | 9/2007 | Bout et al. |
| 7,326,555 | B2 | 2/2008 | Konz, Jr. et al. |
| 8,772,256 | B2 | 7/2014 | Graham |
| 8,932,607 | B2 | 1/2015 | Custers |
| 10,294,279 | B2 | 5/2019 | Langedijk |
| 10,456,462 | B2 | 10/2019 | Langedijk |
| 10,457,708 | B2 | 10/2019 | Langedijk |
| 10,729,757 | B2* | 8/2020 | Langedijk ............... A61P 37/04 |
| 10,899,800 | B2 | 1/2021 | Langedijk |
| 10,953,087 | B2 | 3/2021 | Langedijk |
| 11,034,731 | B2 | 6/2021 | Langedijk |
| 11,155,583 | B2 | 10/2021 | Krarup |
| 11,229,692 | B2 | 1/2022 | Godeaux |
| 11,229,694 | B2 | 1/2022 | Langedijk |
| 11,229,695 | B2 | 1/2022 | Widjojoatmodjo |

(Continued)

FOREIGN PATENT DOCUMENTS

| EP | 0853660 A1 | 7/1998 |
| EP | 1230354 | 8/2002 |

(Continued)

OTHER PUBLICATIONS

Gilman et al., "Rapid profiling of RSV antibody repertoires from the memory B cells of naturally infected adult donors", Science Immunology, 11 pages, Dec. 2016.

Int'l Search Report and Written Opinion dated Dec. 17, 2018 in Int'l Application No. PCT/EP2018/074710, 14 pages.

International Search Report and Written Opinion issued in PCT/EP2017/062875, dated Aug. 14, 2017, 10 pages.

Janssen Vaccines & Prevention B.V.: A Study to Evaluate the Safety, Tolerability and Immunogenicity of Two Vaccinations of Ad26.RSV. preF One Year Apart in Adults Aged 60 Years and Older in Stable Health, Oct. 2016, retrieved from the Internet: http://clinicaltrials.gov/ct2/show/record/NCT02926430 (retrieved on Nov. 30, 2018) 10 pages.

Openshaw et al., "Protective and Harmful Immunity to RSV Infection", Annu Rev. Immunol, vol. 35, pp. 501-532, 2017.

(Continued)

Primary Examiner — Shanon A. Foley
Assistant Examiner — Myron G Hill
(74) Attorney, Agent, or Firm — Ice Miller LLP

(57) ABSTRACT

The present invention relates to novel nucleic acid molecules encoding a pre-fusion RSV F protein or immunologically active part thereof, wherein the pre-fusion RSV F protein comprises the amino acid sequence of SEQ ID NO: 1 or 2. The invention further relates to the use of the nucleic acid molecules, or vectors comprising said nucleic acid molecules, as a vaccine against respiratory syncytial virus (RSV).

1 Claim, 15 Drawing Sheets
Specification includes a Sequence Listing.

(56) References Cited

U.S. PATENT DOCUMENTS

| | | |
|---|---|---|
| 11,338,031 B2 | 5/2022 | Langedijk |
| 2011/0305727 A1 | 12/2011 | Swanson et al. |
| 2012/0164176 A1 | 6/2012 | Swanson et al. |
| 2012/0315270 A1 | 12/2012 | McLellan et al. |
| 2013/0177573 A1 | 7/2013 | Williamson et al. |
| 2014/0073032 A1 | 3/2014 | Custers et al. |
| 2014/0248314 A1 | 9/2014 | Swanson et al. |
| 2014/0271699 A1 | 9/2014 | Kwong |
| 2016/0102123 A1 | 4/2016 | Langedijk |
| 2016/0145321 A1 | 5/2016 | Wadia |
| 2016/0145322 A1 | 5/2016 | Wadia |
| 2016/0176932 A1 | 6/2016 | Langedijk et al. |
| 2020/0061181 A1 | 2/2020 | Godeaux |
| 2020/0197509 A1 | 6/2020 | Widjojoatmodjo et al. |
| 2020/0360506 A1 | 11/2020 | Langedijk |
| 2021/0101940 A1 | 4/2021 | Langedijk |
| 2021/0205440 A1 | 7/2021 | Langedijk |
| 2021/0284698 A1 | 9/2021 | Langedijk |
| 2022/0017574 A1 | 1/2022 | Langedijk |
| 2022/0089652 A1 | 3/2022 | Krarup |
| 2022/0125910 A1 | 4/2022 | Godeaux |
| 2022/0125912 A1 | 4/2022 | Langedijk |
| 2022/0133878 A1 | 5/2022 | Widjojoatmodjo |
| 2022/0193219 A1 | 6/2022 | Callendret |
| 2022/0204567 A1 | 6/2022 | Brandenburg |

FOREIGN PATENT DOCUMENTS

| | | | |
|---|---|---|---|
| JP | 2015512380 | | 4/2015 |
| JP | 2015171378 | | 10/2015 |
| KR | 20140138765 | | 12/2014 |
| WO | 9003184 | A1 | 4/1990 |
| WO | 9014837 | A1 | 12/1990 |
| WO | 96/09378 | A1 | 3/1996 |
| WO | 9611711 | A1 | 4/1996 |
| WO | 98/22588 | A2 | 5/1998 |
| WO | 98/39411 | A1 | 9/1998 |
| WO | 99/12568 | A1 | 3/1999 |
| WO | 99/41416 | A2 | 8/1999 |
| WO | 2000/29024 | A1 | 5/2000 |
| WO | 2000/32754 | A1 | 6/2000 |
| WO | 2000/70071 | A1 | 11/2000 |
| WO | 2001/66137 | A1 | 9/2001 |
| WO | 2001085984 | A1 | 11/2001 |
| WO | 2002/40665 | A2 | 5/2002 |
| WO | 03040178 | A1 | 5/2003 |
| WO | 2003/049763 | A1 | 6/2003 |
| WO | 2003/061708 | A1 | 7/2003 |
| WO | 2003/078592 | A2 | 9/2003 |
| WO | 2003/104467 | A1 | 12/2003 |
| WO | 2004001032 | A2 | 12/2003 |
| WO | 2004004762 | A1 | 1/2004 |
| WO | 2004/020971 | A2 | 3/2004 |
| WO | 2005002620 | A1 | 1/2005 |
| WO | 2005071093 | A2 | 8/2005 |
| WO | 2005/080556 | A2 | 9/2005 |
| WO | 2006/108707 | A1 | 10/2006 |
| WO | 2007/104792 | A2 | 9/2007 |
| WO | 2007/110409 | A1 | 10/2007 |
| WO | 2009/11713 | A1 | 1/2009 |
| WO | 2009079796 | A1 | 7/2009 |
| WO | 2009106580 | A1 | 9/2009 |
| WO | 2010/060719 | A1 | 6/2010 |
| WO | 2010060719 | A1 | 6/2010 |
| WO | 2010086189 | A2 | 8/2010 |
| WO | 2010149743 | A2 | 12/2010 |
| WO | 2010149745 | A1 | 12/2010 |
| WO | 2011008974 | A2 | 1/2011 |
| WO | 2011/020079 | A1 | 2/2011 |
| WO | 2011/045378 | A1 | 4/2011 |
| WO | 2011/045381 | A1 | 4/2011 |
| WO | 2011050168 | A2 | 4/2011 |
| WO | 2011/098592 | A1 | 8/2011 |
| WO | 2012006596 | A2 | 1/2012 |
| WO | 2012158613 | A1 | 11/2012 |
| WO | 2013/139911 | A1 | 9/2013 |
| WO | 2013/139916 | A1 | 9/2013 |
| WO | 2013135615 | A1 | 9/2013 |
| WO | 2014005643 | A1 | 1/2014 |
| WO | 2014077096 | | 5/2014 |
| WO | 2014160463 | A1 | 10/2014 |
| WO | 2014174018 | A1 | 10/2014 |
| WO | 2014202570 | A1 | 12/2014 |
| WO | WO-2014202570 | A1 * | 12/2014 ........... C07K 14/005 |
| WO | 2015013551 | A1 | 1/2015 |
| WO | 2015040002 | A1 | 3/2015 |
| WO | 2015189425 | | 12/2015 |
| WO | 2017174564 | A1 | 10/2017 |
| WO | 2017174568 | | 10/2017 |
| WO | 2021198413 | | 10/2021 |
| WO | 2022002894 | | 1/2022 |

OTHER PUBLICATIONS

U.S. Appl. No. 17/594,394, filed Oct. 14, 2021. Inventor, Benoit Christophe Stephan Callendret.

U.S. Appl. No. 17/595,255, filed Nov. 12, 2021. Inventor, Benoit Christophe Stephan Callendret.

U.S. Appl. No. 17/664,290, filed May 20, 2022, Inventors: Langedijk, Johannes; Verhagen, Janneke M.

Hotard, et al., "Identification of Residues in the Human Respiratory Syncytial Virus Fusion Protein That Modulate Fusion Activity and Pathogenesis," Journal of Virology, vol. 89, No. 1, pp. 512-522, Jan. 2015.

Cohen et al., "Chimpanzee adenovirus CV-68 adapted as a gene delivery vector interacts with the coxsackievirus and adenovirus receptor", Journal of General Virology, 83, pp. 151-155, 2002.

Farina et al., "Replication-Defective Vector Based on a Chimpanzee Adenovirus", Journal of Virology, vol. 75, No. 23, pp. 11603-11613, Dec. 2001.

Kobinger et al., "Chimpanzee adenovirus vaccine protects against Zaire Ebola Virus", Science Direct, Virology, 346, pp. 394-401, 2006.

Lasaro et al., "New Insights on Adenovirus as Vaccine Vectors", Molecular Therapy, vol. 17, No. 8, pp. 1333-1339, Aug. 2009.

Tatsis et al., "A CD46-binding Chimpanzee Adenovirus Vector as a Vaccine Carrier", American Society of Gene Therapy, vol. 15, No. 3, pp. 608-617, Mar. 2007.

Widjojatomodjo et al., "Recombianant Low-seroprevalent adenoviral vectors Ad26 and Ad35 expressing the respiratory syncytial virus (RSV) fusion protein induce protective immunity against RSV infection in cotton rats", Vaccine, 33, pp. 5406-5414, 2015.

Green et al., "Safety and Immunogenicity of novel respiratory syncytial virus (RSV) vaccines based on the RSV viral proteins F, N and M2-1 encoded by simian adenovirus (PanAd3-RSV) and MVA (MVA-RSV): protocol for an open-label, dose-escalation, single-centre, phase 1 clinical trial in healthy adults", BMJ Open, 13 pages, Oct. 2015.

Grunwald et al., "Novel Vaccine Regimen Elicits Strong Airway Immune Responses and Control of Respiratory Syncytial Virus in Nonhuman Primates", Journal of Virology, vol. 88, No. 8, pp. 3997-4007, Apr. 2014.

Comparison to Sequence 16, U.S. Appl. No. 12/517,194; U.S. Pat. No. 8,772,256 (Year: 2014).

McLellan et al., "Structural Basis of Respiratory Syncytial Virus Neutralization by Motavizumab," Nature Structural & Molecular Biology, vol. 17, pp. 248-250 (2010).

McLellan et al., "Structure of RSV Fusion Glycoprotein Trimer Bound to a Prefusion-Specific Neutralizing Antibody," Science, vol. 340, pp. 1113-1117 (2013).

McLellan et al., "Structure-Based Design of a Fusion Glycoprotein Vaccine for Respiratory Syncytial Virus," Science, vol. 342, pp. 592-598 (2013).

Swanson et al., "Structural Basis for Immunization with Postfusion Respiratory Syncytial Virus Fusion F Glycoprotein (RSV F) to Elicit High Neutralizing Antibody Titers," PNAS, vol. 108, pp. 9619-9624 (2011).

(56) References Cited

OTHER PUBLICATIONS

Letarov et al., "The Carboxy-Terminal Domain Initiates Trimerization of Bacteriophage T4 Fibritin," Biochemistry (Moscow), vol. 64, No. 7, pp. 817-823 (1999).
Guthe et al., "Very Fast Folding and Association of a Trimerization Domain from Bacteriophage T4 Fibritin," J. Mol. Biol., vol. 337, pp. 905-915 (2004).
"Database UniProt Accession W8CJC7," http://ibis.internal.epo.org/exam/dbfetch.jsp?id=UNIPROT:W8CJC7, Download date: Aug. 12, 2015, 1 page.
Widjaja et al., "Recombinant soluble Respiratory Syncytial Virus F Protein That Lacks Heptad Repeat B, Contains a GCN4 Trimerization Motif and Is Not Cleaved Displays Prefusion-Like Characteristics," Plos One, 20 pages, Jun. 24, 2015.
Written Opinion dated Oct. 10, 2016 in Int'l Application No. PCT/EP2016/066104.
Int'l Search Report dated Oct. 10, 2016 in Int'l Application No. PCT/EP2016/066104.
Written Opinion dated Oct. 12, 2016 in Int'l Application No. PCT/EP2016/066098.
Int'l Search Report dated Oct. 12, 2016 in Int'l Application No. PCT/EP2016/066098.
Suzuki et al., "An Isoleucine Zipper Peptide Forms a Native-like Triple Stranded Coiled Coil in Solution," Protein Engineering, vol. 11, No. 11, pp. 1051-1055 (1998).
Dames et al., "NMR Structure of a Parallel Homotrimeric Coiled Coil," Nature Structural Biology, vol. 5, No. 8, pp. 687-691 (Aug. 1998).
Calder et al., "Electron Microscopy of the Human Respiratory Syncytial Virus Fusion Protein and Complexes That It Forms With Monoclonal Antibodies," Virology, vol. 271, pp. 122-131 (2000).
Harbury et al., "A Switch Between Two-, Three-, and Four-Stranded Coiled Coils in GON4 Leucine Zipper Mutants," Science, vol. 262, pp. 1401-1407.
O'Shea et al., "Evidence That the Leucine Zipper Is a Coiled Coil," Science, vol. 243, pp. 538-542 (Jan. 27, 1989).
Database EMBL, Aug. 28, 1995, Human respiratory syncytial virus, strain RSB89-1734, fusion protein (F) mRNA, complete CDS, XP002729919.
Int'l Search Report and Written Opinion dated Oct. 9, 2014 in Int'l Application No. PCT/EP2014/062655.
Int'l Search Report and Written Opinion dated Aug. 12, 2014 in Int'l Application No. PCT/EP2014/058353.
Magro et al., "Neutralizing Antibodies Against the Preactive Form of Respiratory Syncytial Virus Protein Offer Unique Possibilities for Clinical Intervention," PNAS, vol. 109, No. 8, pp. 3089-3094 (Feb. 21, 2012).
Yin et al., "Structure of the Parainfluenza Virus 5 F Protein in its Metastable, Prefusion Conformation," Nature, vol. 439, pp. 38-44 (Jan. 5, 2006).
Ngwuta et al, "Prefusion F-Specific Antibodies Determine the Magnitude of RSV Neutralizing Activity in Human Sera," Science Translational Medicine, vol. 7, No. 309, pp. 1-9 (2015).
Int'l Search Report and Written Opinion dated Jun. 12, 2017 in Int'l Application No. PCT/EP2017/057962.
Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).
Abrahamsen et al, "Construction of an Adenovirus Type 7a E1A-Vector," Journal of Virology, vol. 71, No. 11, pp. 8946-8951 (Nov. 1997).
Altaras et al, "Production and Formulation of Adenovirus Vectors," Advances in Biochemical Engineering / Biotechnology, vol. 99, pp. 193-260 (2005).
Brough et al, "A Gene Transfer Vector-Cell Line System for Complete Functional Complementation of Adenovirus Early Regions E1 and E4," Journal of Virology, vol. 70, No. 9, pp. 6497-6501 (Sep. 1996).
Fallaux et al, "New Helper Cells and Matched Early Region 1-Deleted Adenovirus Vectors Prevent Generation of Replication-Competent Adenoviruses," Human Gene Therapy, vol. 9, pp. 1909-1917 (Sep. 1998).
Gao et al, "A Cell Line for High-Yield Production of E1-Deleted Adenovirus Vectors without the Emergence of Replication-Competent Virus," Human Gene Therapy, vol. 11, pp. 213-219 (Jan. 2000).
Goerke et al, "Development of a Novel Adenovirus Purification Process Utilizing Selective Precipitation of Cellular DNA," Biotechnology and Bioengineering, vol. 91, pp. 12-21 (2005).
Havenga et al, "Novel replication-incompetent adenoviral B-group vectors: high vector stability and yield in PER.C6 cells," Journal of General Virology, vol. 87, pp. 2135-2143 (2006).
Hoganson et al, "Development of a Stable Adenoviral Vector Formulation," BioProcessing Journal, vol. 1, No. 1, pp. 43-48 (Mar. 2002).
Kim et al, "Single mucosal immunization of recombinant adenovirus-based vaccine expressing F1 protein fragment induces protective mucosal immunity against respiratory syncytial virus infection," Vaccine, vol. 28, pp. 3801-3808 (2010).
Kohlmann et al, "Protective Efficacy and Immunology of an Adenoviral Vector Vaccine Encoding the Codon-Optimized F Protein of Respiratory Syncytial Virus," Journal of Virology, vol. 83, No. 23, pp. 12601-12610 (Dec. 2009).
Konz et al, "Serotype Specificity of Adenovirus Purification Using Anion-Exchange Chromatography," Human Gene Therapy, vol. 16, pp. 1346-1353 (Nov. 2005).
Konz et al, "Scaleable Purification of Adenovirus Vectors," Methods in Molecular Biology, vol. 434, No. 2, pp. 13-23 (2008).
Krarup et al, "A Highly Stable Prefusion RSV F Vaccine Derived from Structural Analysis of the Fusion Mechanism," Nature Communications, vol. 6, pp. 1-11 (Sep. 2015).
Nan et al, "Development of an Ad7 cosmid system and generation of an Ad7LE1LE3HIVMN env/rev recombinant virus," Gene Therapy, vol. 10, pp. 326-336 (2003).
Pemberton et al, "Cytoxic T Cell Specificity for Respiratory Syncytial Virus Proteins: Fusion Protein is an Important Target Antigen," Journal of General Virology, vol. 68, pp. 2177-2182 (1987).
Solabomi et al, "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (Aug. 2008).
Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).
Yu et al., "Single Intranasal Immunization with Recombinant Adenovirus-Based Vaccine Induces Protective Immunity against Respiratory Syncytial Virus Infection," Journal of Virology, vol. 82, No. 5, pp. 2350-2357 (Mar. 2008).
Int'l Search Report and Written Opinion dated Jun. 12, 2017 in Int'l Application No. PCT/EP2017/057957.
Krause et al, "A Broadly Neutralizing Human Monclonal Antibody That Recognizes a Conserved, Novel Epitope on the Globular Head of the Influenza H1N1 Virus Hemagglutinin," Journal of Virology, vol. 85, No. 20, pp. 10905-10908 (Oct. 2011).
McLellan et al, "Structure of Respiratory Syncytial Virus Fusion Glycoprotein in the Postfusion Conformation Reveals Preservation of Neutralizing Epitopes," Journal of Virology, vol. 85, No. 15, pp. 7788-7796 (Aug. 2011).
Database Geneseq (online) "RSV fusion protein N671 S215P, RSV CL57-v224, fibritin, SEQ: 74", XP002761983, retrieved from EBI accession No. GSP:BBP75438, Database accession No. BBP75438 sequence.
Neuzil, "Progress toward a Respiratory Syncytial Virus Vaccine", Clinical and Vaccine Immunology, vol. 23, pp. 186-188, 2016.
Int'l Search Report and Written Opinion dated Sep. 8, 2018 in Int'l Application No. PCT/EP2018/062604.
Bangari et al., "Development of nonhuman adenoviruses as vaccine vectors", Vaccine, 24(7), pp. 849-862, 2006.

(56) References Cited

OTHER PUBLICATIONS

D. Roymans et al: "Binding of a potent small-molecule inhibitor of six-helix bundle formation requires interactions with both heptad-repeats of the RSV fusion protein", Proceedings of the National Academy of Sciences, vol. 107, No. 1, Dec. 4, 2009 (Dec. 4, 2009), pp. 308-313, XP055708078,ISSN: 0027-8424, DOI: 10.1073/pnas.0910108106.

\* cited by examiner

SEQUENCE LISTING

<160> NUMBER OF SEQ ID NOS: 6

<210> SEQ ID NO 1
<211> LENGTH: 574
<212> TYPE: PRT
<213> ORGANISM: Artificial Sequence
<220> FEATURE:
<223> OTHER INFORMATION: RSV preF2.1 amino acid sequence

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp

```
                   355                 360                 365
Thr Met Asn Ser Leu Thr Leu Pro Ser Glu Val Asn Leu Cys Asn Val
            370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu His Asn Val Asn Ala Val Lys Ser Thr Thr Asn Ile Met Ile Thr
        515                 520                 525
Thr Ile Ile Ile Val Ile Ile Val Ile Leu Leu Ser Leu Ile Ala Val
    530                 535                 540
Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
                565                 570

<210> SEQ ID NO 2
<211> LENGTH: 574
<212> TYPE: PRT
<213> ORGANISM: Artificial Sequence
<220> FEATURE:
<223> OTHER INFORMATION: RSV preF2.2 amino acid sequence

<400> SEQUENCE: 2

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Glu Ile Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Arg Ala Arg Arg Glu Leu Pro
            100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
    130                 135                 140
Gly Ser Ala Ile Ala Ser Gly Val Ala Val Ser Lys Val Leu His Leu
```

-continued

```
            145                 150                 155                 160
    Glu Gly Glu Val Asn Lys Ile Lys Ser Ala Leu Leu Ser Thr Asn Lys
                    165                 170                 175
    Ala Val Val Ser Leu Ser Asn Gly Val Ser Val Leu Thr Ser Lys Val
                    180                 185                 190
    Leu Asp Leu Lys Asn Tyr Ile Asp Lys Gln Leu Leu Pro Ile Val Asn
                    195                 200                 205
    Lys Gln Ser Cys Ser Ile Pro Asn Ile Glu Thr Val Ile Glu Phe Gln
                    210                 215                 220
    Gln Lys Asn Asn Arg Leu Leu Glu Ile Thr Arg Glu Phe Ser Val Asn
    225                 230                 235                 240
    Ala Gly Val Thr Thr Pro Val Ser Thr Tyr Met Leu Thr Asn Ser Glu
                    245                 250                 255
    Leu Leu Ser Leu Ile Asn Asp Met Pro Ile Thr Asn Asp Gln Lys Lys
                    260                 265                 270
    Leu Met Ser Asn Asn Val Gln Ile Val Arg Gln Gln Ser Tyr Ser Ile
                    275                 280                 285
    Met Ser Ile Ile Lys Glu Glu Val Leu Ala Tyr Val Val Gln Leu Pro
    290                 295                 300
    Leu Tyr Gly Val Ile Asp Thr Pro Cys Trp Lys Leu His Thr Ser Pro
    305                 310                 315                 320
    Leu Cys Thr Thr Asn Thr Lys Glu Gly Ser Asn Ile Cys Leu Thr Arg
                    325                 330                 335
    Thr Asp Arg Gly Trp Tyr Cys Asp Asn Ala Gly Ser Val Ser Phe Phe
                    340                 345                 350
    Pro Gln Ala Glu Thr Cys Lys Val Gln Ser Asn Arg Val Phe Cys Asp
                    355                 360                 365
    Thr Met Asn Ser Leu Thr Leu Pro Ser Glu Val Asn Leu Cys Asn Val
                    370                 375                 380
    Asp Ile Phe Asn Pro Lys Tyr Asp Cys Lys Ile Met Thr Ser Lys Thr
    385                 390                 395                 400
    Asp Val Ser Ser Ser Val Ile Thr Ser Leu Gly Ala Ile Val Ser Cys
                    405                 410                 415
    Tyr Gly Lys Thr Lys Cys Thr Ala Ser Asn Lys Asn Arg Gly Ile Ile
                    420                 425                 430
    Lys Thr Phe Ser Asn Gly Cys Asp Tyr Val Ser Asn Lys Gly Val Asp
                    435                 440                 445
    Thr Val Ser Val Gly Asn Thr Leu Tyr Tyr Val Asn Lys Gln Glu Gly
                    450                 455                 460
    Lys Ser Leu Tyr Val Lys Gly Glu Pro Ile Ile Asn Phe Tyr Asp Pro
    465                 470                 475                 480
    Leu Val Phe Pro Ser Asn Glu Phe Asp Ala Ser Ile Ser Gln Val Asn
                    485                 490                 495
    Glu Lys Ile Asn Gln Ser Leu Ala Phe Ile Arg Lys Ser Asp Glu Leu
                    500                 505                 510
    Leu His Asn Val Asn Ala Val Lys Ser Thr Thr Asn Ile Met Ile Thr
                    515                 520                 525
    Thr Ile Ile Ile Val Ile Val Ile Leu Leu Ser Leu Ile Ala Val
                    530                 535                 540
    Gly Leu Leu Leu Tyr Cys Lys Ala Arg Ser Thr Pro Val Thr Leu Ser
    545                 550                 555                 560
    Lys Asp Gln Leu Ser Gly Ile Asn Asn Ile Ala Phe Ser Asn
                    565                 570
```

<210> SEQ ID NO 3
<211> LENGTH: 1725
<212> TYPE: DNA
<213> ORGANISM: Artificial Sequence
<220> FEATURE:
<223> OTHER INFORMATION: codon optimized nucleic acid encoding the RSV F
      pre-F2.1 pre-fusion protein

<400> SEQUENCE: 3

| | | | |
|---|---|---|---|
| atggagctgc tgatcctgaa ggccaacgcc atcaccacca tcctgaccgc cgtgaccttc | 60 |
| tgcttcgcca gcggccagaa catcaccgag gagttctacc agagcacctg cagcgccgtg | 120 |
| agcaagggct acctgggcgc cctgagaacc ggctggtaca ccagcgtgat caccatcgag | 180 |
| ctgagcaaca tcaaggagat caagtgcaac ggcaccgacg ccaaggtgaa gctgatcaag | 240 |
| caggagctgg acaagtacaa gaacgccgtg accgagctgc agctgctgat gcagagcacc | 300 |
| cccgccacca acaacagagc cagaagagag ctgcccagat tcatgaacta caccctgaac | 360 |
| aacgccaaga gaccaacgt gaccctgagc aagaagagaa agaagatt cctgggcttc | 420 |
| ctgctgggcg tgggcagcgc catcgccagc ggcgtggccg tgagcaaggt gctgcacctg | 480 |
| gagggcgagt gaacaagat caagagcgcc ctgctgagca ccaacaaggc cgtggtgagc | 540 |
| ctgagcaacg gcgtgagcgt gctgaccagc aaggtgctgg acctgaagaa ctacatcgac | 600 |
| aagcagctgc tgcccatcgt gaacaagcag agctgcagca tccccaacat cgagaccgtg | 660 |
| atcgagttcc agcagaagaa caacagactg ctggagatca ccagagagtt cagcgtgaac | 720 |
| gccggcgtga ccacccccgt gagcacctac atgctgacca cagcgagct gctgagcctg | 780 |
| atcaacgaca tgcccatcac caacgaccag aagaagctga tgagcaacaa cgtgcagatc | 840 |
| gtgagacagc agagctacag catcatgagc atcatcaagg aggaggtgct ggcctacgtg | 900 |
| gtgcagctgc ccctgtacgg cgtgatcgac accccctgct ggaagctgca caccagcccc | 960 |
| ctgtgcacca ccaacaccaa ggagggcagc aacatctgcc tgaccagaac cgacagaggc | 1020 |
| tggtactgcg acaacgccgg cagcgtgagc ttcttccccc aggccgagac tgcaaggtg | 1080 |
| cagagcaaca gagtgttctg cgacaccatg aacagcctga ccctgcccag cgaggtgaac | 1140 |
| ctgtgcaacg tggacatctt caaccccaag tacgactgca agatcatgac cagcaagacc | 1200 |
| gacgtgagca gcagcgtgat caccagcctg ggcgccatcg tgagctgcta cggcaagacc | 1260 |
| aagtgcaccg ccagcaacaa gaacagaggc atcatcaaga ccttcagcaa cggctgcgac | 1320 |
| tacgtgagca caagggcgt ggacaccgtg agcgtgggca caccctgta ctacgtgaac | 1380 |
| aagcaggagg gcaagagcct gtacgtgaag ggcgagccca tcatcaactt ctacgacccc | 1440 |
| ctggtgttcc ccagcgacga gttcgacgcc agcatcagcc aggtgaacga gaagatcaac | 1500 |
| cagagcctgg ccttcatcag aaagagcgac gagctgctgc acaacgtgaa cgccgtgaag | 1560 |
| agcaccacca acatcatgat caccaccatc atcatcgtga tcatcgtgat cctgctgagc | 1620 |
| ctgatcgccg tgggcctgct gctgtactgc aaggccagaa gcacccccgt gacccctgagc | 1680 |
| aaggaccagc tgagcggcat caacaacatc gccttcagca actga | 1725 |

<210> SEQ ID NO 4
<211> LENGTH: 1725
<212> TYPE: DNA
<213> ORGANISM: Artificial Sequence
<220> FEATURE:
<223> OTHER INFORMATION: codon optimized nucleic acid encoding the RSV F
      pre-F2.2 pre-fusion protein

<400> SEQUENCE: 4

```
atggagctgc tgatcctgaa ggccaacgcc atcaccacca tcctgaccgc cgtgaccttc    60
tgcttcgcca gcggccagaa catcaccgag gagttctacc agagcacctg cagcgccgtg   120
agcaagggct acctgagcgc cctgagaacc ggctggtaca ccagcgtgat caccatcgag   180
ctgagcaaca tcaaggagat caagtgcaac ggcaccgacg ccaaggtgaa gctgatcaag   240
caggagctgg acaagtacaa gaacgccgtg accgagctgc agctgctgat gcagagcacc   300
cccgccacca caacagagc cagaagagag ctgcccagat tcatgaacta caccctgaac   360
aacgccaaga gaccaacgt gaccctgagc aagaagagaa agagaagatt cctgggcttc   420
ctgctgggcg tgggcagcgc catcgccagc ggcgtggccg tgagcaaggt gctgcacctg   480
gagggcgagg tgaacaagat caagagcgcc ctgctgagca ccaacaaggc cgtggtgagc   540
ctgagcaacg gcgtgagcgt gctgaccagc aaggtgctgg acctgaagaa ctacatcgac   600
aagcagctgc tgcccatcgt gaacaagcag agctgcagca tccccaacat cgagaccgtg   660
atcgagttcc agcagaagaa caacagactg ctggagatca ccagagagtt cagcgtgaac   720
gccggcgtga ccacccccgt gagcacctac atgctgacca cagcgagct gctgagcctg   780
atcaacgaca tgcccatcac caacgaccag aagaagctga tgagcaacaa cgtgcagatc   840
gtgagacagc agagctacag catcatgagc atcatcaagg aggaggtgct ggcctacgtg   900
gtgcagctgc ccctgtacgg cgtgatcgac accccctgct ggaagctgca caccagcccc   960
ctgtgcacca ccaacaccaa ggagggcagc aacatctgcc tgaccagaac cgacagaggc  1020
tggtactgcg acaacgccgg cagcgtgagc ttcttccccc aggccgagac ctgcaaggtg  1080
cagagcaaca gagtgttctg cgacaccatg aacagcctga ccctgcccag cgaggtgaac  1140
ctgtgcaacg tggacatctt caaccccaag tacgactgca gatcatgac cagcaagacc  1200
gacgtgagca gcagcgtgat caccagcctg ggcgccatcg tgagctgcta cggcaagacc  1260
aagtgcaccg ccagcaacaa gaacagaggc atcatcaaga ccttcagcaa cggctgcgac  1320
tacgtgagca caagggcgt ggacaccgtg agcgtgggca caccctgta ctacgtgaac  1380
aagcaggagg gcaagagcct gtacgtgaag ggcgagccca tcatcaactt ctacgacccc  1440
ctggtgttcc ccagcaacga gttcgacgcc agcatcagcc aggtgaacga aagatcaac  1500
cagagcctgg ccttcatcag aaagagcgac gagctgctgc acaacgtgaa cgccgtgaag  1560
agcaccacca acatcatgat caccaccatc atcatcgtga tcatcgtgat cctgctgagc  1620
ctgatcgccg tgggcctgct gctgtactgc aaggccagaa gcaccccgt gaccctgagc  1680
aaggaccagc tgagcggcat caacaacatc gccttcagca actga              1725
```

<210> SEQ ID NO 5
<211> LENGTH: 6
<212> TYPE: DNA
<213> ORGANISM: Artificial Sequence
<220> FEATURE:
<223> OTHER INFORMATION: Kozak sequence

<400> SEQUENCE: 5

```
gccacc                                                                 6
```

```
<210> SEQ ID NO 6
<211> LENGTH: 6
<212> TYPE: DNA
<213> ORGANISM: Artificial Sequence
<220> FEATURE:
<223> OTHER INFORMATION: synthetic sequence encoding two stop codons

<400> SEQUENCE: 6 tgataa                                                                6
```

VACCINE AGAINST RSV

CROSS-REFERENCE TO RELATED APPLICATIONS

This application is a continuation of U.S. patent application Ser. No. 16/946,485 filed Jun. 24, 2020, which is a continuation of U.S. patent application Ser. No. 16/091,257, filed Oct. 4, 2018, which is a Section 371 of International Application No. PCT/EP2017/057957, filed Apr. 4, 2017, which was published in the English language on Oct. 12, 2017, under International Publication No. WO 2017/174564 A1, which claims priority under 35 U.S.C. § 119(b) to European Application No. 16163807.7, filed Apr. 5, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence_Listing_004852-111US3", creation date of May 12, 2022, and having a size of about 16 KB. The sequence listing submitted via EFS-Web is part of the specification and is herein incorporated by reference in its entirety.

FIELD OF THE INVENTION

The invention relates to the field of medicine. More in particular, the invention relates to vaccines against RSV.

BACKGROUND OF THE INVENTION

Respiratory syncytial virus (RSV) is a highly contagious childhood pathogen of the respiratory tract which is believed to be responsible for 200,000 childhood deaths annually. In children younger than 2 years, RSV accounts for approximately 50% of the hospitalizations due to respiratory infections, with a peak of hospitalization occurring at 2-4 months of age. It has been reported that almost all children will have experienced infection with RSV by the age of two, and repeated infection during life is attributed to low natural immunity. In the elderly, the RSV disease burden is similar to those caused by non-pandemic influenza A infections. A vaccine against RSV is currently not available, but is desired due to the high disease burden.

RSV is a paramyxovirus, belonging to the subfamily of pneumovirinae. Its genome encodes for various proteins, including the membrane proteins known as RSV Glycoprotein (G) and RSV fusion (F) protein which are the major antigenic targets for neutralizing antibodies.

Unlike the RSV G protein, the F protein is conserved between RSV strains; which makes it an attractive vaccine candidate able to elicit broadly neutralizing antibodies. The F protein is a transmembrane protein and it is incorporated in the virion membrane from cellular membrane during virus budding. The RSV F protein facilitates infection by fusing the viral and host-cell membranes. In the process of fusion, the F protein refolds irreversibly from a labile pre-fusion conformation to a stable post-fusion conformation. The protein precursor, F0, requires cleavage during intracellular maturation by a furin-like protease. There are two furin sites, cleavage of which results in removal of a p27 peptide and formation of two domains: an N-terminal F2 domain and a C-terminal F1 domain (FIG. 1). The F2 and F1 domains are connected by two cystine bridges. Antibodies against the fusion protein can prevent virus uptake in the cell and thus have a neutralizing effect. Besides being a target for neutralizing antibodies, RSV F contains cytotoxic T cell epitopes (Pemberton et al, 1987, J. Gen. Virol. 68: 2177-2182).

Despite 50 years of research, there is still no licensed vaccine against RSV. One major obstacle to the vaccine development is the legacy of vaccine-enhanced disease in a clinical trial in the 1960s with a formalin-inactivated (FI) RSV vaccine. FI-RSV vaccinated children were not protected against natural infection and infected children experienced more severe illness than non-vaccinated children, including two deaths. This phenomenon is referred to as 'enhanced disease'.

Since the trial with the FI-RSV vaccine, various approaches to generate an RSV vaccine have been pursued. Attempts include classical live attenuated cold passaged or temperature sensitive mutant strains of RSV, (chimeric) protein subunit vaccines, peptide vaccines and RSV proteins expressed from recombinant viral vectors, including adenoviral vectors. Although some of these vaccines showed promising pre-clinical data, no vaccine has been licensed for human use due to safety concerns or lack of efficacy.

Therefore, a need remains for efficient vaccines and methods of vaccinating against RSV, in particular vaccines that do not lead to enhanced disease. The present invention aims at providing such vaccines and methods for vaccinating against RSV in a safe and efficacious manner.

SUMMARY OF THE INVENTION

The present invention provides novel nucleic acid molecules encoding stable RSV pre-fusion F proteins, wherein the RSV pre-fusion F proteins comprise the amino acid sequence of SEQ ID NO: 1 or 2.

In certain embodiments, the nucleic acid molecules encoding the RSV pre-fusion F proteins are codon optimized for expression in human cells.

In certain embodiments, the nucleic acid molecules encoding the RSV pre-fusion F proteins comprise the nucleic acid sequence of SEQ ID NO: 3 or 4.

The invention further provides vectors comprising the nucleic acid molecules encoding RSV pre-fusion F proteins, wherein the RSV F protein comprises the amino acid sequence of SEQ ID NO: 1 or 2.

In certain embodiments, the vector is a human recombinant adenovirus.

In certain embodiments, the recombinant adenovirus is of serotype 26 or 35.

In certain embodiments, the recombinant human adenovirus has a deletion in the E1 region, a deletion in the E3 region, or a deletion in both the E1 and the E3 region of the adenoviral genome.

In certain embodiments, the recombinant adenovirus has a genome comprising at its 5' terminal ends the sequence CTATCTAT.

The invention also provides compositions, e.g. vaccines against respiratory syncytial virus (RSV), comprising a nucleic acid molecule or a vector according to the invention.

The invention further provides a method for vaccinating a subject against RSV, the method comprising administering to the subject a composition according to the invention.

In certain embodiments, the method of vaccinating a subject against RSV further comprises administering RSV F protein (preferably formulated as a pharmaceutical composition, thus a protein vaccine) to the subject.

The invention also provides a method for reducing infection and/or replication of RSV in, e.g. the nasal tract and lungs of, a subject, comprising administering to the subject a composition comprising a nucleic acid or vector according to the invention. This will reduce adverse effects resulting from RSV infection in a subject, and thus contribute to protection of the subject against such adverse effects upon administration of the composition. In certain embodiments, adverse effects of RSV infection may be essentially prevented, i.e. reduced to such low levels that they are not clinically relevant.

The invention also provides an isolated host cell comprising a nucleic acid molecule encoding a RSV pre-fusion F protein, wherein the RSV pre-fusion F protein comprises the amino acid sequence of SEQ ID NO: 1 or 2. In certain embodiments, the nucleic acid molecule encoding the RSV pre-fusion F protein comprises the nucleic acid sequence of SEQ ID NO: 3 or 4.

The invention further provides a method for making a vaccine against respiratory syncytial virus (RSV), comprising providing a recombinant human adenovirus that comprises nucleic acid encoding a RSV pre-fusion F protein or fragment thereof, propagating said recombinant adenovirus in a culture of host cells, isolating and purifying the recombinant adenovirus, and formulating the recombinant adenovirus in a pharmaceutically acceptable composition, wherein the RSV pre-fusion F protein comprises the amino acid sequence of SEQ ID NO: 1 or 2. In certain embodiments, the recombinant adenovirus is of serotype 26 or 35.

BRIEF DESCRIPTION OF THE FIGURES

(FIG. 5A) The percentage of cells positive for the staining was determined. (FIG. 5B) The Mean Fluorescent Intensity (MFI) values were calculated and normalized to MFI of 37 C cell sample. The MFI of 37° C. sample was set to 1. Dotted lines correspond to background staining at 60° C.

(FIG. 8A) Virus neutralizing antibodies were determined against RSV A Long using a micro-neutralization assay with an ELISA based read out. Titers are given as the log 2 value of the IC50. (FIG. 8B) Pre-fusion or post-fusion F antibody titers were determined by ELISA, and the ratio between pre- and post-fusion F antibodies for all samples that showed pre- and post-fusion F titers above lower limit of quantification (LLoQ) was calculated. (FIG. 8C) Subclass ELISA was performed using post-fusion RSV F A2 as coating reagent, and the IgG2a/IgG1 ratio (log 10) is plotted. Ratio's observed for Th1 (serum derived from animals immunized with RSV F expression Adenoviral vectors) and Th2 (serum derived from FI-RSV immunized animals) references samples are indicated with dashed lines. The LLoQ is indicated with a dotted lines (panels A), and horizontal bars represent the mean responses per group.

Ad26.RSV.FA2 (n=3) or Ad26.RSV.preF (n=4) or formulation buffer (n=2) were used in virus neutralization assays (micro-neutralization assay with an ELISA based read out) with the RSV A (upper panels) and B strains (lower panels) indicated. Titers are given as the log 2 value of the IC50, and horizontal bars represent the mean response per group. LLoQ is indicated with a dashed line.

FIGS. 10A, 10B, 10C, 10D, 10E, and 10F: Single immunization with Ad26.RSV.preF2.2 or Ad35.RSV.preF2.2 at low doses protects cotton rats against challenge with the homologous RSV A2. Cotton rats (*Sigmodon hispidus*) (n=7 to 9 per group) were immunized with the indicated doses (in vp/animal) of Ad26.RSV.preF2.2, Ad26.RSV.FA2 (left panels), Ad35.RSV.preF2.2 or Ad35.RSV.FA2 (right panels) by single intramuscular administration. Control immunizations were performed with formulation buffer, FI-RSV, or intranasal application of a low dose of RSV A2. At seven weeks post-immunization animals were challenged intranasally with 105 pfu RSV A2. The lung (FIGS. 10A and 10B) and nose viral titers (FIGS. 10C and 10D) were determined by plaque assay 5 days after challenge. (FIGS. 10E and 10F) Sera taken just before challenge were used to perform a virus neutralizing assay with the RSV A Long strain (micro-neutralization assay with an ELISA based read out). The dotted line represents the lower level of quantification (LLoQ). Horizontal bars represent the mean titer per group.

Figure 11:
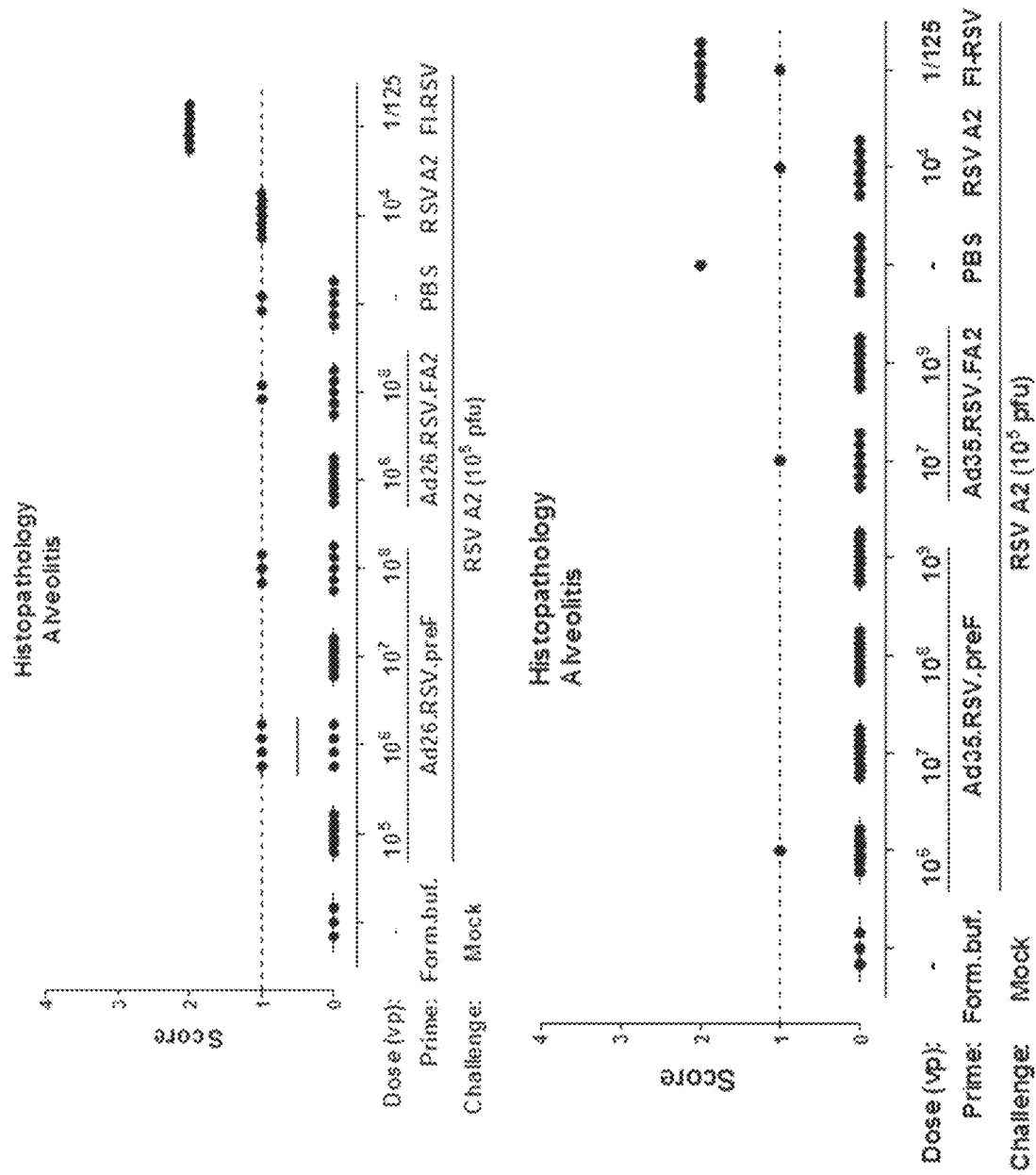

FIG. 11: Ad26.RSV.preF2.2 or Ad35.RSV.preF2.2 immunization of cotton rats does not result in increased alveolitis scores after RSV A2 challenge. Cotton rats (*Sigmodon hispidus*) (n=7 to 9 per group) were immunized with the indicated doses (in vp/animal) of Ad26.RSV.preF2.2, Ad26.RSV.FA2 (upper panel), Ad35.RSV.preF2.2, or Ad35.RSV.FA2 (lower panel) by single intramuscular administration. Control immunizations were performed with formulation buffer, FI-RSV, or intranasal application of a low dose of RSV A2. At seven weeks post-immunization animals were challenged intranasally with 105 pfu RSV A2. Alveolitis was scored by histopathological examination of one lung lobe 5 days after challenge on a non-linear scale from 0 to 4. The horizontal dotted line marks the maximal score of the control animals that were pre-exposed to RSV-A2 before challenge to mimic a natural exposure to RSV that does not lead to ERD.

DETAILED DESCRIPTION OF THE INVENTION

RSV vaccines comprising human adenovirus comprising nucleic acid encoding RSV F protein have previously been described in WO2013/139911 and WO2013/139916. It was shown therein that recombinant adenoviruses of serotype 26 or 35 that comprise a nucleic acid encoding an RSV F protein are very effective vaccines against RSV in a well established cotton rat model and have improved efficacy as compared to data described earlier for Ad5 encoding RSV F protein. It was demonstrated that a single administration, even administered intramuscularly, of Ad26 or Ad35 encoding RSV F is sufficient to provide complete protection against challenge RSV replication.

Because of the instability of the RSV F protein, however, the RSV F protein has the propensity to prematurely refold into its more stable post-fusion conformation. This phenomenon is an intrinsic feature of the protein both in solution and on the surface of the virions. In human sera most RSV neutralizing antibodies are, however, directed against the RSV F in the pre-fusion conformation. In the research that led to the present invention, effort was therefore undertaken to identify modifications that stabilize RSV F protein in its pre-fusion conformation in the full length protein.

Several possible mutations stabilizing RSV F protein in the pre-fusion conformation have previously been described in WO2014/174018 and WO2014/202570. The nucleic acid molecules according to the present invention encode RSV F proteins comprising a unique and specific subset of mutations. According to the invention it has been shown that this unique combination of mutations of the present invention results in increased RSV F protein expression levels and stability of the RSV F protein in the pre-fusion conformation. In addition, it has been shown that the nucleic acid molecules according to the invention encode RSV F protein which is stabilized in the pre-fusion conformation, and which induces higher titers of neutralizing antibody as compared to wild type RSV F protein (as disclosed in WO2013/139911 and WO2013/139916).

In a first aspect, the present invention thus provides novel nucleic acid molecules encoding a pre-fusion respiratory syncytial virus F protein (RSV pre-fusion F protein, or RSV pre-F protein), wherein the RSV pre-F protein comprises the amino acid sequence of SEQ ID NO: 1 or 2.

In certain embodiments, the nucleic acid molecules encode the RSV pre-F proteins of SEQ ID NO: 1 or SEQ ID NO: 2.

As used herein, the terms nucleic acid, nucleic acid molecule, nucleic acid or nucleotide sequence, and polynucleotide are used interchangeably and all refer to the linear biopolymers (chains) made from nucleotides, including DNA and RNA.

It is understood by a skilled person that numerous different nucleic acid molecules can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleic acid molecule encoding an amino acid sequence" includes all nucleotide sequences that are degenerate versions of each other and that encode the same amino acid sequence. Nucleotide sequences that encode proteins and RNA may include introns. Sequences herein are provided from 5' to 3' direction, as custom in the art.

In certain embodiments, the nucleic acid molecule encodes a fragment of pre-fusion RSV F comprising the amino acid sequence of SEQ ID NO: 1 or 2.

In certain embodiments, the nucleic acid molecules encoding the RSV pre-fusion F protein, or fragment thereof, are codon optimized for expression in mammalian cells, such as human cells. Methods of codon-optimization are known and have been described previously (e.g. WO 96/09378).

In certain embodiments, the nucleic acid molecule encoding the RSV pre-fusion F protein comprises the nucleic acid sequence of SEQ ID NO: 3. In certain embodiments, the nucleic acid encoding the RSV F protein comprises the nucleic acid sequence of SEQ ID NO: 4.

In certain embodiments, the nucleic acid encoding the RSV F protein consists of the nucleic acid sequence of SEQ ID NO: 3 or 4.

The term "fragment" as used herein refers to a peptide that has an amino-terminal and/or carboxy-terminal and/or internal deletion, but where the remaining amino acid sequence is identical to the corresponding positions in the sequence of the full length RSV F protein, for example, the RSV F protein of SEQ ID NO. 1 or 2. It will be appreciated that for inducing an immune response and in general for vaccination purposes, a protein needs not to be full length nor have all its wild type functions, and fragments of the protein are equally useful. The person skilled in the art will also appreciate that changes can be made to a protein, e.g. by amino acid substitutions, deletions, additions, etc, e.g. using routine molecular biology procedures. Generally, conservative amino acid substitutions may be applied without loss of function or immunogenicity of a polypeptide. This can easily be checked according to routine procedures well known to the skilled person.

The present invention also relates to vectors comprising a nucleic acid molecule encoding a pre-fusion RSV F protein comprising the amino acid sequence of SEQ ID NO: 1 or 2, or a fragment thereof.

According to the invention, the vector may be any vector that can be conveniently subjected to recombinant DNA procedures and can bring about expression of the nucleic acid molecule of the invention. The choice of the vector will typically depend on the compatibility of the vector with the host cell into which the vector is to be introduced.

In certain embodiments, the vector is a human recombinant adenovirus, also referred to as recombinant adenoviral vectors. The preparation of recombinant adenoviral vectors is well known in the art. The term 'recombinant' for an adenovirus, as used herein implicates that it has been modified by the hand of man, e.g. it has altered terminal ends actively cloned therein and/or it comprises a heterologous gene, i.e. it is not a naturally occurring wild type adenovirus.

In certain embodiments, an adenoviral vector according to the invention is deficient in at least one essential gene function of the E1 region, e.g. the E1a region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region).

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in *Virology*, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual*, 2d ed., Cold Spring Harbor Press, Cold Spring Harbor, N.Y. (1989), Watson et al., *Recombinant DNA*, 2d ed., Scientific American Books (1992), and Ausubel et al., *Current Protocols in Molecular Biology*, Wiley Interscience Publishers, NY (1995), and other references mentioned herein.

In certain embodiments, the adenovirus is a human adenovirus of the serotype 26 or 35. The vaccines according to the invention based on these serotypes appear more potent than the ones described in the prior art that were based on Ad5, since those failed to provide complete protection against RSV challenge replication after a single intramuscular administration (Kim et al, 2010, Vaccine 28: 3801-3808; Kohlmann et al, 2009, *J Virol* 83: 12601-12610; Krause et al, 2011, *Virology Journal* 8:375). The serotype of the invention further generally has a low seroprevalence and/or low preexisting neutralizing antibody titers in the human population. Recombinant adenoviral vectors of these serotypes with different transgenes are evaluated in clinical trials, and thus far shows to have an excellent safety profile. Preparation of rAd26 vectors is described, for example, in WO 2007/104792 and in Abbink et al., (2007) *Virol* 81(9): 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., (2003) *J Virol* 77(15): 8263-71. Exemplary genome sequences of Ad35 are found in GenBank Accession AC_000019 and in FIG. 6 of WO 00/70071.

A recombinant adenovirus according to the invention may be replication-competent or replication-deficient. In certain embodiments, the adenovirus is replication deficient, e.g. because it contains a deletion in the E1 region of the genome. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as 'packaging cell' or 'complementing cell' or 'host cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al, 2000, *Human Gene Therapy* 11: 213-219), 293, and the like. In certain embodiments, the producer cells are for instance HEK293 cells, or PER.C6 cells, or 911 cells, or IT293SF cells, and the like.

For non-subgroup C E1-deficient adenoviruses such as Ad35 (subgroup B) or Ad26 (subgroup D), it is preferred to exchange the E4-orf6 coding sequence of these non-subgroup C adenoviruses with the E4-orf6 of an adenovirus of subgroup C such as Ad5. This allows propagation of such adenoviruses in well known complementing cell lines that express the E1 genes of Ad5, such as for example 293 cells or PER.C6 cells (see, e.g. Havenga et al, 2006, *J. Gen. Virol.* 87: 2135-2143; WO 03/104467, incorporated in its entirety by reference herein). In certain embodiments, an adenovirus that can be used is a human adenovirus of serotype 35, with a deletion in the E1 region into which the nucleic acid encoding RSV F protein antigen has been cloned, and with an E4 orf6 region of Ad5. In certain embodiments, the adenovirus in the vaccine composition of the invention is a human adenovirus of serotype 26, with a deletion in the E1 region into which the nucleic acid encoding RSV F protein antigen has been cloned, and with an E4 orf6 region of Ad5.

In alternative embodiments, there is no need to place a heterologous E4orf6 region (e.g. of Ad5) in the adenoviral vector, but instead the E1-deficient non-subgroup C vector is propagated in a cell line that expresses both E1 and a compatible E4orf6, e.g. the 293-ORF6 cell line that expresses both E1 and E4orf6 from Ad5 (see e.g. Brough et al, 1996, *J Virol* 70: 6497-501 describing the generation of the 293-ORF6 cells; Abrahamsen et al, 1997, *J Virol* 71: 8946-51 and Nan et al, 2003, *Gene Therapy* 10: 326-36 each describing generation of E1 deleted non-subgroup C adenoviral vectors using such a cell line).

Alternatively, a complementing cell that expresses E1 from the serotype that is to be propagated can be used (see e.g. WO 00/70071, WO 02/40665).

For subgroup B adenoviruses, such as Ad35, having a deletion in the E1 region, it is preferred to retain the 3' end of the E1B 55K open reading frame in the adenovirus, for instance the 166 bp directly upstream of the pIX open reading frame or a fragment comprising this such as a 243 bp fragment directly upstream of the pIX start codon (marked at the 5' end by a Bsu36I restriction site in the Ad35 genome), since this increases the stability of the adenovirus because the promoter of the pIX gene is partly residing in this area (see, e.g. Havenga et al, 2006, *J. Gen. Virol.* 87: 2135-2143; WO 2004/001032, incorporated by reference herein).

"Heterologous nucleic acid" (also referred to herein as 'transgene') in adenoviruses of the invention is nucleic acid that is not naturally present in the adenovirus. It is introduced into the adenovirus for instance by standard molecular biology techniques. In the present invention, the heterologous nucleic acid encodes the RSV pre-F protein (or fragment thereof) comprising the amino acid sequence of SEQ ID NO: 1 or 2. It can for instance be cloned into a deleted E1 or E3 region of an adenoviral vector. A transgene is generally operably linked to expression control sequences. This can for instance be done by placing the nucleic acid encoding the transgene(s) under the control of a promoter. Further regulatory sequences may be added. Many promoters can be used for expression of a transgene(s), and are known to the skilled person. A non-limiting example of a suitable promoter for obtaining expression in eukaryotic cells is a CMV-promoter (U.S. Pat. No. 5,385,839), e.g. the CMV immediate early promoter, for instance comprising nt. −735 to +95 from the CMV immediate early gene enhancer/promoter. A polyadenylation signal, for example the bovine growth hormone polyA signal (U.S. Pat. No. 5,122,458), may be present behind the transgene(s).

In certain embodiments, the recombinant adenovectors of the invention comprise as the 5' terminal nucleotides the nucleotide sequence: CTATCTAT. These embodiments are advantageous because such vectors display improved replication in production processes, resulting in batches of adenovirus with improved homogeneity, as compared to vectors having the original 5' terminal sequences (generally CATCATCA) (see also patent application nos. PCT/EP2013/054846 and U.S. Ser. No. 13/794,318, entitled 'Batches of recombinant adenovirus with altered terminal ends' filed on 12 Mar. 2012 in the name of Crucell Holland B.V.), incorporated in its entirety by reference herein. The invention thus also provides batches of recombinant adenovirus encoding RSV F protein or a part thereof, wherein the RSV F protein comprises the amino acid sequence of SEQ ID NO: 1 or 2, and wherein essentially all (e.g. at least 90%) of the adenoviruses in the batch comprise a genome with terminal nucleotide sequence CTATCTAT.

In certain embodiments, the nucleic acid molecule may encode a fragment of the pre-fusion F protein of RSV. The fragment may result from either or both of amino-terminal and carboxy-terminal deletions. The extent of deletion may be determined by a person skilled in the art to, for example, achieve better yield of the recombinant adenovirus. The fragment will be chosen to comprise an immunologically active fragment of the F protein, i.e. a part that will give rise to an immune response in a subject. This can be easily determined using in silico, in vitro and/or in vivo methods, all routine to the skilled person.

The invention furthermore provides compositions comprising a nucleic acid molecule encoding a pre-fusion RSV F comprising the amino acid sequence of SEQ ID NO: 1 or 2.

Also, the invention provides compositions comprising a vector as described herein.

In certain embodiments, the compositions comprising a nucleic acid molecule and/or a vector are for use in reducing infection and/or replication of RSV in a subject. In certain preferred embodiments, the compositions are for use as a vaccine against RSV. The term "vaccine" refers to an agent or composition containing an active component effective to induce a therapeutic degree of immunity in a subject against a certain pathogen or disease. In the present invention, the vaccine comprises an effective amount of a nucleic acid molecule that encodes an RSV pre-fusion F protein comprising SEQ ID NO: 1 or 2, or an antigenic fragment thereof, which results in an immune response against the F protein of RSV. This provides a method of preventing serious lower respiratory tract disease leading to hospitalization and the decrease the frequency of complications such as pneumonia and bronchiolitis due to RSV infection and replication in a subject. Thus, the invention also provides a method for preventing or reducing serious lower respiratory tract disease, preventing or reducing (e.g. shortening) hospitalization, and/or reducing the frequency and/or severity of pneumonia or bronchiolitis caused by RSV in a subject, comprising administering to the subject a composition comprising a nucleic acid molecule encoding a RSV pre-F protein or fragment thereof, wherein the RSV F protein comprises the amino acid sequence of SEQ ID NO: 1 or 2. The term "vaccine" according to the invention implies that it is a pharmaceutical composition, and thus typically includes a pharmaceutically acceptable diluent, carrier or excipient. It may or may not comprise further active ingredients. In certain embodiments it may be a combination vaccine that further comprises other components that induce an immune response, e.g. against other proteins of RSV and/or against other infectious agents.

In certain embodiments the compositions comprising the nucleic acid molecule or vector further comprise, or are administered together with, one or more adjuvants. Adjuvants are known in the art to further increase the immune response to an applied antigenic determinant, and pharmaceutical compositions comprising adenovirus and suitable adjuvants are for instance disclosed in WO 2007/110409, incorporated by reference herein. The terms "adjuvant" and "immune stimulant" are used interchangeably herein, and are defined as one or more substances that cause stimulation of the immune system. In this context, an adjuvant is used to enhance an immune response to the RSV prefusion F proteins of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057, 540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like. It is also possible to use vector-encoded adjuvant, e.g. by using heterologous nucleic acid that encodes a fusion of the oligomerization domain of C4-binding protein (C4 bp) to the antigen of interest (e.g. Solabomi et al, 2008, Infect Immun 76: 3817-23). In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

In other embodiments, the compositions do not comprise adjuvants.

It is also possible according to the invention to administer further active components, in combination with the compositions, e.g. vaccines, according to the invention. Such further active components may comprise e.g. other RSV antigens or vectors comprising nucleic acid encoding these. Such vectors again may be non-adenoviral or adenoviral, of which the latter can be of any serotype. An example of other RSV antigens includes RSV F or G protein or immunologically active parts thereof. For instance, intranasally applied recombinant replication-deficient Ad5 based adenovector rAd/3×G, expressing the soluble core domain of G glycoprotein (amino acids 130 to 230) was protective in a murine model (Yu et al, 2008, J Virol 82: 2350-2357), and although it was not protective when applied intramuscularly, it is clear from these data that RSV G is a suitable antigen for inducing protective responses. Further active components may also comprise non-RSV antigens, e.g. from other pathogens such as viruses, bacteria, parasites, and the like. The administration of further active components may for instance be done by separate administration or by administering combination products of the vaccines of the invention and the further active components. In certain embodiments, further non-adenoviral antigens (besides RSV.F), may be encoded in the vectors of the invention. In certain embodiments, it may thus be desired to express more than one protein from a single adenovirus, and in such cases more coding sequences for instance may be linked to form a single transcript from a single expression cassette or may be present in two separate expression cassettes cloned in different parts of the adenoviral genome.

The compositions of the invention, e.g. the adenovirus compositions, may be administered to a subject, e.g. a human subject. The total dose of the adenovirus provided to a subject during one administration can be varied as is known to the skilled practitioner, and is generally between 1×10^7 viral particles (vp) and 1×10^12 vp, preferably between 1×10^8 vp and 1×10^11 vp, for instance between 3×10^8 and 5×10^10 vp, for instance between 10^9 and 3×10^10 vp.

Administration of the compositions can be performed using standard routes of administration. Non-limiting embodiments include parenteral administration, such as by injection e.g. intradermal, intramuscular, etc, or subcutaneous, transcutaneous, or mucosal administration, e.g. intranasal, oral, and the like. Intranasal administration has generally been seen as a preferred route for vaccines against RSV. The most important advantage of the live intrasal strategy is the direct stimulation of local respiratory tract immunity and the lack of associated disease enhancement. The only vaccines under clinical evaluation for pediatric use at the present time are live intranasal vaccine (Collins and Murphy. Vaccines against human respiratory syncytial virus). In: Perspectives in Medical Virology 14: Respiratory Syncytial Virus (Ed. Cane, P.), Elsevier, Amsterdam, the Netherlands, pp 233-277). Intranasal administration is a suitable preferred route according to the present invention as well. The advantage of intramuscular administration is that it is simple and well-established, and does not carry the safety concerns for intranasal application in infants younger than 6 months. In one embodiment a composition is administered by intramuscular injection, e.g. into the deltoid muscle of the arm, or vastus lateralis muscle of the thigh. The skilled person knows the various possibilities to administer a composition, e.g. a vaccine in order to induce an immune response to the antigen(s) in the vaccine.

A subject as used herein preferably is a mammal, for instance a rodent, e.g. a mouse, a cotton rat, or a non-human-primate, or a human. Preferably, the subject is a human subject. The subject can be of any age, e.g. from about 1 month to 100 years old, e.g. from about 2 months to about 80 years old, e.g. from about 1 month to about 3 years old, from about 3 years to about 50 years old, from about 50 years to about 75 years old, etc.

It is also possible to provide one or more booster administrations of one or compositions, e.g. the vaccines, of the invention. If a boosting vaccination is performed, typically, such a boosting vaccination will be administered to the same subject at a moment between one week and one year, preferably between two weeks and four months, after administering the composition to the subject for the first time (which is in such cases referred to as 'priming vaccination'). In alternative boosting regimens, it is also possible to administer different vectors, e.g. one or more adenoviruses of different serotype, or other vectors such as MVA, or DNA, or protein, to the subject after the priming vaccination. It is for instance possible to administer to the subject a recombinant adenoviral vector comprising a nucleic acid sequence encoding the pre-fusion RSV F protein as a prime, and to boost with a composition comprising a RSV F protein. In certain embodiments, the RSV F protein also is stabilized in the pre-fusion conformation.

In certain embodiments, the administration comprises a priming and at least one booster administration. In certain embodiments, the composition is administered as a priming composition and/or as a boosting composition in a prime-boost vaccination regimen. In certain embodiments thereof, the priming administration is with a rAd35 comprising nucleic acid encoding RSV pre-F protein or a fragment thereof (rAd35-RSV.pre-F'), wherein the RSV F pre-F protein comprises the amino acid sequence of SEQ ID NO: 1 or 2, and the booster administration is with a rAd26 comprising nucleic acid encoding RSV F protein (rAd26-RSV.pre-F'), wherein the RSV pre-F protein comprises the amino acid sequence of SEQ ID NO: 1 or 2. In other embodiments thereof, the priming administration is with rAd26-RSV.pre-F and the booster administration is with rAd35-RSV.pre-F. In other embodiments, both the priming and booster administration are with rAd26.RSV.pre-F. In certain embodiments, the priming administration is with rAd26-RSV.pre-F or rAd35-RSV.pre-F and the booster administration is with RSV F protein. In all these embodiments, it is possible to provide further booster administrations with the same or other vectors or protein. Embodiments where boosting with RSV F protein may be particularly beneficial include e.g. in elder subjects in risk groups (e.g. having COPD or asthma) of 50 years or older, or e.g. in healthy subjects of 60 years or older or 65 years or older.

In certain embodiments, the administration comprises a single administration of a composition according to the invention, without further (booster) administrations. Such embodiments are advantageous in view of the reduced complexity and costs of a single administration regimen as compared to a prime-boost regimen. Complete protection is already observed after single administration of the recombinant adenoviral vectors of the invention without booster administrations in the cotton rat model in the examples herein.

In a further aspect, the invention provides methods for making a vaccine against respiratory syncytial virus (RSV), comprising providing a recombinant human adenovirus that comprises nucleic acid encoding a RSV F protein or fragment thereof, propagating said recombinant adenovirus in a culture of host cells, isolating and purifying the recombinant adenovirus, and bringing the recombinant adenovirus in a pharmaceutically acceptable composition, wherein the RSV F protein comprises the amino acid sequence of SEQ ID NO: 1 or 2.

Recombinant adenovirus can be prepared and propagated in host cells, according to well known methods, which entail cell culture of the host cells that are infected with the adenovirus. The cell culture can be any type of cell culture, including adherent cell culture, e.g. cells attached to the surface of a culture vessel or to microcarriers, as well as suspension culture.

Most large-scale suspension cultures are operated as batch or fed-batch processes because they are the most straightforward to operate and scale up. Nowadays, continuous processes based on perfusion principles are becoming more common and are also suitable (see e.g. WO 2010/060719, and WO 2011/098592, both incorporated by reference herein, which describe suitable methods for obtaining and purifying large amounts of recombinant adenoviruses).

Producer cells are cultured to increase cell and virus numbers and/or virus titers. Culturing a cell is done to enable it to metabolize, and/or grow and/or divide and/or produce virus of interest according to the invention. This can be accomplished by methods as such well known to persons skilled in the art, and includes but is not limited to providing nutrients for the cell, for instance in the appropriate culture media. Suitable culture media are well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Typically, the adenovirus will be exposed to the appropriate producer cell in a culture, permitting uptake of the virus. Usually, the optimal agitation is between about 50 and 300 rpm, typically about 100-200, e.g. about 150, typical DO is 20-60%, e.g. 40%, the optimal pH is between 6.7 and 7.7, the optimal temperature between 30 and 39° C., e.g. 34-37° C., and the optimal MOI between 5 and 1000, e.g. about 50-300. Typically, adenovirus infects producer cells spontaneously, and bringing the producer cells into contact with rAd particles is sufficient for infection of the cells. Generally, an adenovirus seed stock is added to the culture to initiate infection, and subsequently the adenovirus propagates in the producer cells. This is all routine for the person skilled in the art.

After infection of an adenovirus, the virus replicates inside the cell and is thereby amplified, a process referred to herein as propagation of adenovirus. Adenovirus infection results finally in the lysis of the cells being infected. The lytic characteristics of adenovirus therefore permits two different modes of virus production. The first mode is harvesting virus prior to cell lysis, employing external factors to lyse the cells. The second mode is harvesting virus supernatant after (almost) complete cell lysis by the produced virus (see e.g. U.S. Pat. No. 6,485,958, describing the harvesting of adenovirus without lysis of the host cells by an external factor). It is preferred to employ external factors to actively lyse the cells for harvesting the adenovirus.

Methods that can be used for active cell lysis are known to the person skilled in the art, and have for instance been discussed in WO 98/22588, p. 28-35. Useful methods in this respect are for example, freeze-thaw, solid shear, hypertonic and/or hypotonic lysis, liquid shear, sonication, high pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents that can be used, and the way they are employed, are generally known to the person skilled in the art. Several examples are for instance discussed in WO 98/22588, p. 29-33. Detergents can include anionic, cationic, zwitterionic, and nonionic detergents. The concentration of the detergent may be varied, for instance within the range of about 0.1%-5% (w/w). In one embodiment, the detergent used is Triton X-100.

Nuclease may be employed to remove contaminating, i.e. mostly from the producer cell, nucleic acids. Exemplary nucleases suitable for use in the present invention include Benzonase®, Pulmozyme®, or any other DNase and/or RNase commonly used within the art. In preferred embodiments, the nuclease is Benzonase®, which rapidly hydrolyzes nucleic acids by hydrolyzing internal phosphodiester bonds between specific nucleotides, thereby reducing the viscosity of the cell lysate. Benzonase® can be commercially obtained from Merck KGaA (code W214950). The concentration in which the nuclease is employed is preferably within the range of 1-100 units/ml. Alternatively, or in addition to nuclease treatment, it is also possible to selectively precipitate host cell DNA away from adenovirus preparations during adenovirus purification, using selective precipitating agents such as domiphen bromide (see e.g. U.S. Pat. No. 7,326,555; Goerke et al., 2005, Biotechnology and bioengineering, Vol. 91: 12-21; WO 2011/045378; WO 2011/045381).

Methods for harvesting adenovirus from cultures of producer cells have been extensively described in WO 2005/080556.

In certain embodiments, the harvested adenovirus is further purified. Purification of the adenovirus can be performed in several steps comprising clarification, ultrafiltration, diafiltration or separation with chromatography as described in for instance WO 05/080556, incorporated by reference herein. Clarification may be done by a filtration step, removing cell debris and other impurities from the cell lysate. Ultrafiltration is used to concentrate the virus solution. Diafiltration, or buffer exchange, using ultrafilters is a way for removal and exchange of salts, sugars and the like. The person skilled in the art knows how to find the optimal conditions for each purification step. Also WO 98/22588, incorporated in its entirety by reference herein, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Preferably, purification employs at least one chromatography step, as for instance discussed in WO 98/22588, p. 61-70. Many processes have been described for the further purification of adenoviruses, wherein chromatography steps are included in the process. The person skilled in the art will be aware of these processes, and can vary the exact way of employing chromatographic steps to optimize the process. It is for instance possible to purify adenoviruses by anion exchange chromatography steps, see for instance WO 2005/080556 and Konz et al, 2005, *Hum Gene Ther* 16: 1346-1353. Many other adenovirus purification methods have been described and are within the reach of the skilled person. Further methods for producing and purifying adenoviruses are disclosed in for example (WO 00/32754; WO 04/020971; U.S. Pat. Nos. 5,837,520; 6,261,823; WO 2006/108707; Konz et al, 2008, *Methods Mol Biol* 434: 13-23; Altaras et al, 2005, *Adv Biochem Eng Biotechnol* 99: 193-260), all incorporated by reference herein.

For administering to humans, the invention may employ pharmaceutical compositions comprising the rAd and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The purified rAd preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g pH 5.0 to 7.5. The rAd typically is in a solution having a suitable pharmaceutically acceptable buffer, and the solution of rAd may also contain a salt. Optionally stabilizing agent may be present, such as albumin. In certain embodiments, detergent is added. In certain embodiments, rAd may be formulated into an injectable preparation. These formulations contain effective amounts of rAd, are either sterile liquid solutions, liquid suspensions or lyophilized versions and optionally contain stabilizers or excipients. An adenovirus vaccine can also be aerosolized for intranasal administration (see e.g. WO 2009/117134).

For instance, adenovirus may be stored in the buffer that is also used for the Adenovirus World Standard (Hoganson et al, Development of a stable adenoviral vector formulation, *Bioprocessing* March 2002, p. 43-48): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Obviously, many other buffers can be used, and several examples of suitable formulations for the storage and for pharmaceutical administration of purified (adeno)virus preparations can for instance be found in European patent no. 0853660, U.S. Pat. No. 6,225,289 and in international patent applications WO 99/41416, WO 99/12568, WO 00/29024, WO 01/66137, WO 03/049763, WO 03/078592, WO 03/061708.

The invention is further explained in the following examples. The examples do not limit the invention in any way. They merely serve to clarify the invention.

EXAMPLES

Example 1. Stabilizing the RSV F Protein in its Pre Fusion Conformation

Plasmids encoding basic RSV F sequences were synthesized and the amino acid substitutions were introduced in the protein by site-directed mutagenesis. The protein variants were transiently expressed in HEK293 cells. The relative protein expression on the cell surface was assessed by Flow Cytometry. The stability of the F proteins in pre-fusion conformation was evaluated in a heat-stability assay.

The protein sequence used for RSV A2 F protein variants was retrieved from the GenBank, accession number ACO83301.1. The amino acid substitutions were introduced in the sequence by site-directed mutagenesis (QuikChange II XL Site-Directed Mutagenesis Kit, Agilent technologies). The mutagenesis primers were designed using on-line tool PrimerX. HEK293T cells (CRL-11268) were purchased from American Tissue Culture Collection and cultured under standard cell culture conditions (37° C., 10% CO2).

Fully human IgG1 anti-RSV F protein antibodies CR9501 and CR9503 were constructed by cloning the heavy (VH) and light (VL) chain variable regions into a single IgG1 expression vector. PER.C6® cells (Crucell) were transfected with the IgG1 expression constructs and the expressed antibodies were purified from culture supernatants using POROS Mabcapture A chromatography (Applied Biosystems) and then buffer exchanged to 50 mM NaAc, 50 mM NaCl, pH 5.5. Antibody concentration was measured by optical absorption at 280 nm. Antibody quality was also confirmed by size-exclusion chromatography (SEC), SDS-PAGE and isoelectric focusing. The antibody CR9501 comprises VH and VL regions of 58C5 (as described in WO2011/020079) which binds specifically to RSV F protein in its pre-fusion conformation and not to the post-fusion conformation. CR9503 comprises VH and VL regions of motavizumab, which recognizes both the pre-fusion and post-fusion conformation of RSV F.

Protein Expression and Temperature Treatment:

The plasmids were transiently transfected into adherent HEK293T cells using 293fectine (Cat #12347-019) transfection reagents (Life Technologies) according to suppliers recommendations. 48 hours post transfection the cells were harvested by detaching with EDTA-containing FACS buffer (no trypsin, see next section) and cell suspension was heat-treated for 10 minutes either in a water bath or in PCR block for the temperature stability experiments. After the heat-treatment, the cells were prepared for the Flow Cytometry analysis.

For analysis of adeno expressed F proteins, A549 cells were infected with Ad26 virus at a MOI of 10 000 or 5000 and Ad35 viruses at a MOI of 5000, 2500 or 1.250. After 48h, the cells were detached and heat treated for 15 minutes at 37° C., 50° C. and 56° C. Upon heat treatment cells were stained using CR9501-Alexa647 or CR9503-Alexa647 and Propidium Iodide (PI). After staining, the cells were fixed and analyzed using the BD FACS CANTO II cell analyzer.

Flow Cytometry Analysis:

For each staining, the following controls were included: 1) negative control sample. i.e. cells that were not subjected to any treatment and not stained with any antibody labeled with a fluorophore; 2) positive control samples, i.e. cells that are stained with only one fluorophore (one of each that are used for the experiment).

The cells were resuspended in the Flow Cytometry (FC Buffer, 5 mM EDTA, 1% FBS in PBS) and distributed in volumes of 50 µl of the cell suspension per well in a 96-well plate with a lid (U- or V-bottom plates). Two-step or one-step protocols were used for staining.

In case of the two-step protocol 50 µl of the first Abs (or buffer for negative controls) was added to the wells and incubated at RT for 30 min. Biotinylated CR9501 and CR9503 were used at 2 µg/ml (final concentration in a well 1 µg/ml). After incubation, the cells were washed 2 times with the FC buffer. Afterwards 50 µl of Streptavidin-APC (Molecular Probes cat #SA1005, 0.1 mg/ml is used at 1:100) or buffer for negative controls was added to the wells and incubated at RT for 30 min. The cells were washed again 2 times with the FC buffer. After the last wash, the cells were resuspended in 100 µl of FC buffer+/−live-dead stain (PI from Invitrogen, cat #P1304MP, used at 2 µg/ml) and incubated at RT for 15 minutes. The cells were centrifuged at 200 g (1000 rpm) for 5 min., the buffer with PI was removed and the cells were resuspended in 150 µl of the FC buffer.

In case of a one-step protocol, CR9501 and CR9503 antibodies were labeled with fluorescent probe Alexa647 (Molecular Probes, cat #A-20186) according to manufacturer's instructions. Cells were stained according to the protocol above excluding the Streptavidin-APC step.

From the live cell population, the percentage of cells positive for CR9501/CR9503 antibody binding was determined. The cells positive for CR9503 binding express RSV F protein on their surface. The cells positive for CR9501 binding express pre-fusion RSV F on their surface.

The intensity of the antibody staining (Median fluorescence intensity—MFI) is proportional to the amount of F protein on the cell surface. MFI was calculated from the live cell population expressing F protein.

Results:

Surface Cell Expression of the Full Length F Protein Variants:

A subset of mutations that was previously identified to increase expression or stability of the RSV F protein ectodomain in pre-fusion conformation was introduced in the wild type full length RSV A2 F sequence (accession number Genbank ACO83301). The mutations were introduced alone or in multiple combinations, and the effect on protein expression and stability was assessed.

Figure 1:
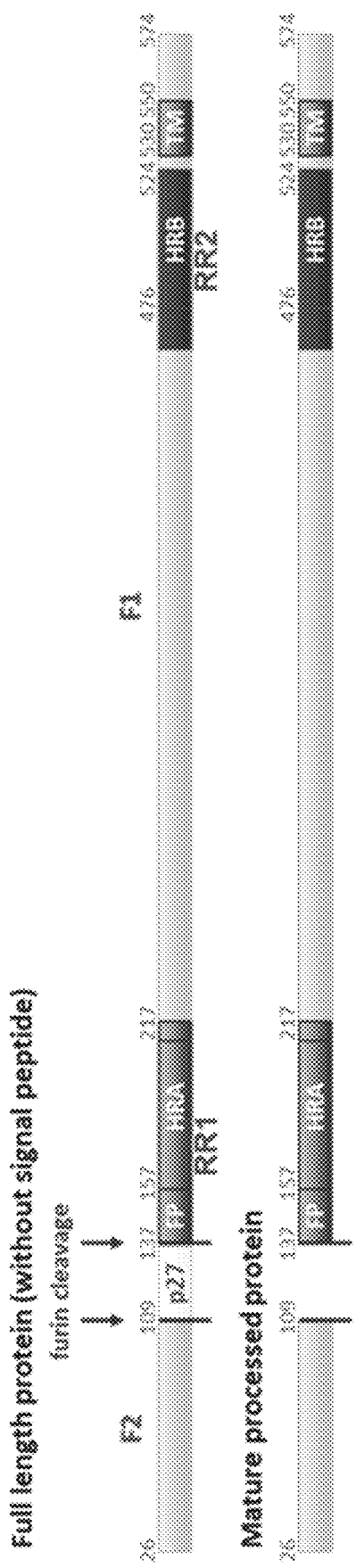
FIG. 1: Schematic representation of the RSV F protein. A protein precursor includes F2 and F1 domains and p27 peptide that is removed from the mature proteins by cleavage with furin-like proteases. The cleavage sites are indicated by arrows. The numbers on top of the boxes indicate amino acid positions in the full length protein excluding signal peptide. In the F1, structural elements are shown: fusion peptide (FP), refolding region 1 (RR1) including heptad repeat A (HRA) and refolding region 2 (RR2) including heptad repeat B (HRB).
Figure 2:
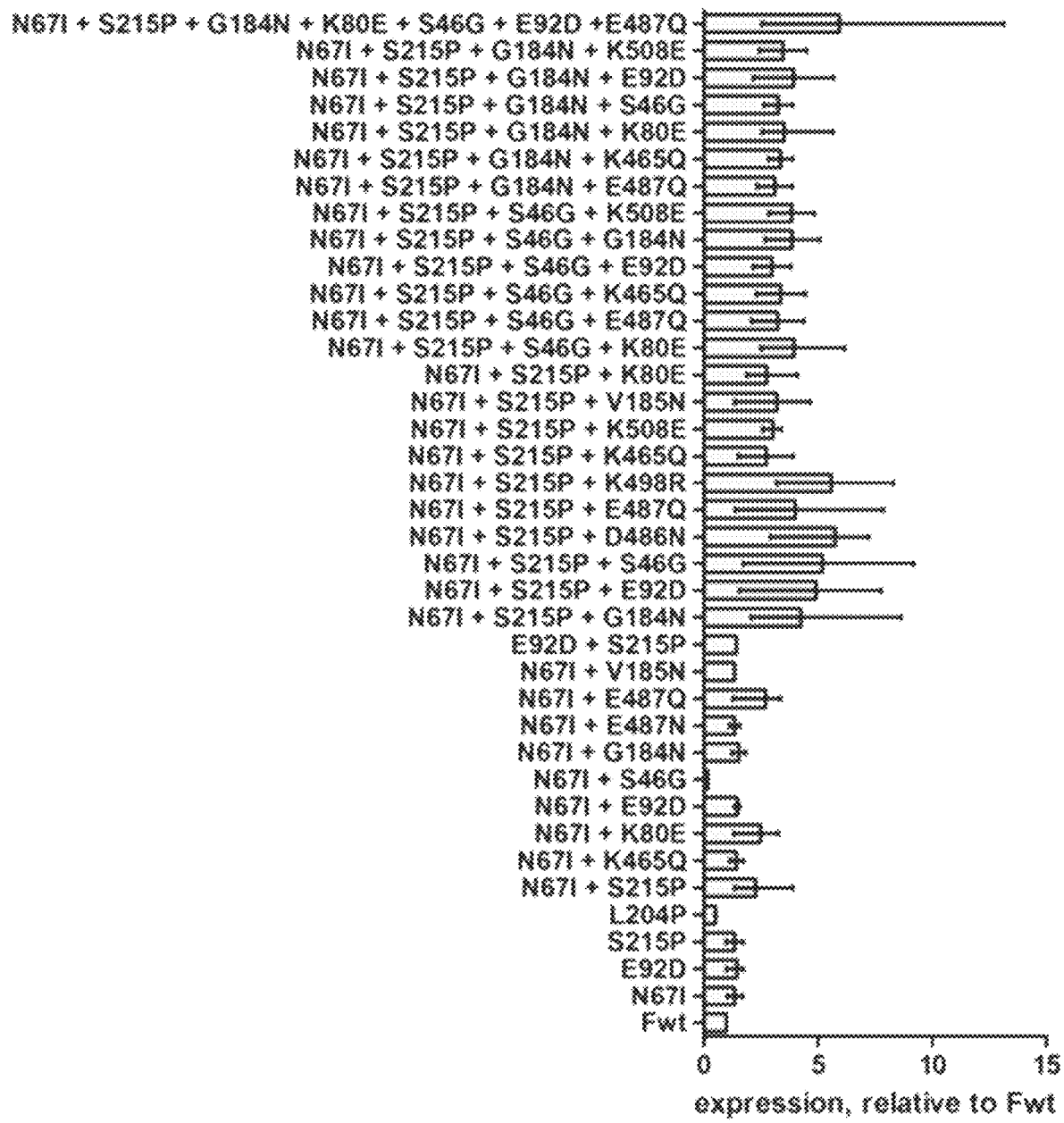
FIG. 2: Relative surface expression of F protein variants. Full length variants of F protein were expressed in HEK293T cells. The cell were stained with anti-RSV F antibody (CR9503) and analyzed by Flow Cytometry (FACS). The Mean Fluorescent Intensity (MFI) values were calculated and normalized to MFI of control F wild type (Fwt)-transfected cell sample. The MFI of Fwt was set to 1. Bars represent mean values, error bars represent range of values.

The expression level of the protein was measured as mean fluorescence intensity (MFI) by Flow Cytometry after staining with the CR9503 antibody that is recognizing both pre-fusion and post-fusion F protein. The combination of the two amino acid substitutions that were previously described for stabilization of the soluble RSV pre-F protein (i.e. N67I and S215P) also increased the expression level of the full length RSV F protein by 2.3-fold, relative to wild type full length RSV F (FIG. 2).

A prominent increase in expression was observed for variants with 3 amino acid substitutions combined. Interestingly, combination of more than three mutations in one variant did not further increase protein expression. This may be due to limited capacity of the cellular membrane to accommodate multiple copies of F protein.

Figure 3:
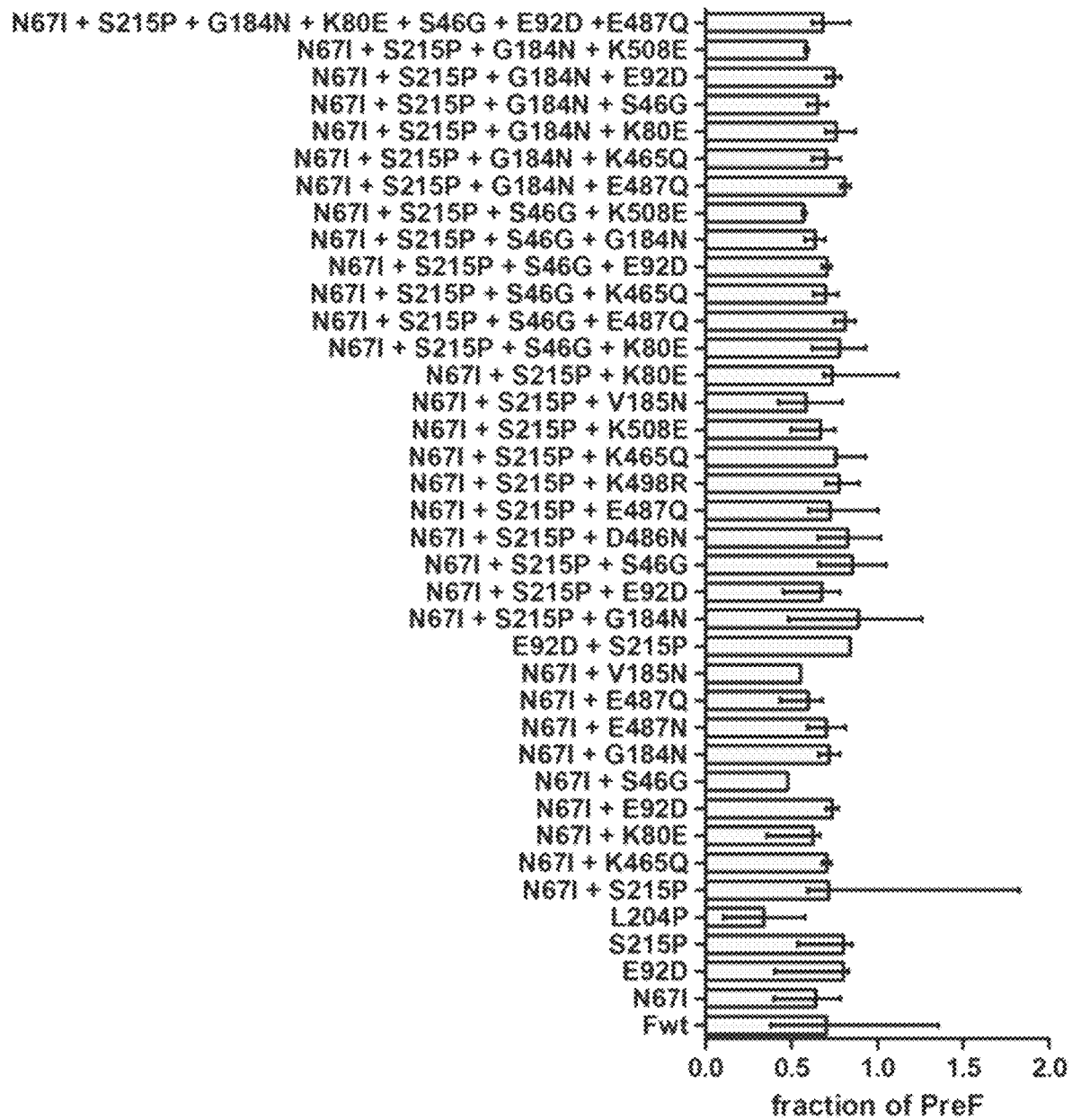
FIG. 3: Fraction of pre-fusion F protein on cell surface. Full length variants of F protein were expressed in HEK293T cells. The cell were stained with anti-RSV F antibody CR9503 and anti-pre-fusion RSV F antibody CR9501 and analyzed by Flow Cytometry. The Mean Fluorescent Intensity (MFI) values were calculated and MFI measured by CR9501 was normalized to MFI measured by CR9503. The normalized MFI values indicate fraction of the pre-F on the cell surface. Bars represent mean values, error bars represent range of values.

The amount of the pre-fusion F on the surface of the cell was assessed by staining with pre-fusion specific antibody CR9501 (FIG. 3). Transfection of the cells with all F variants resulted in a more or less similar amount of pre-fusion F protein on the cell surface. Presence of the transmembrane domain stabilizes the full length protein to certain extent and therefore differences in the pre-fusion stability are not as apparent under ambient conditions between the full length F proteins. Therefore the heat-stability assay was developed to better discriminate stability of full length variants, as described below.

Figure 4:
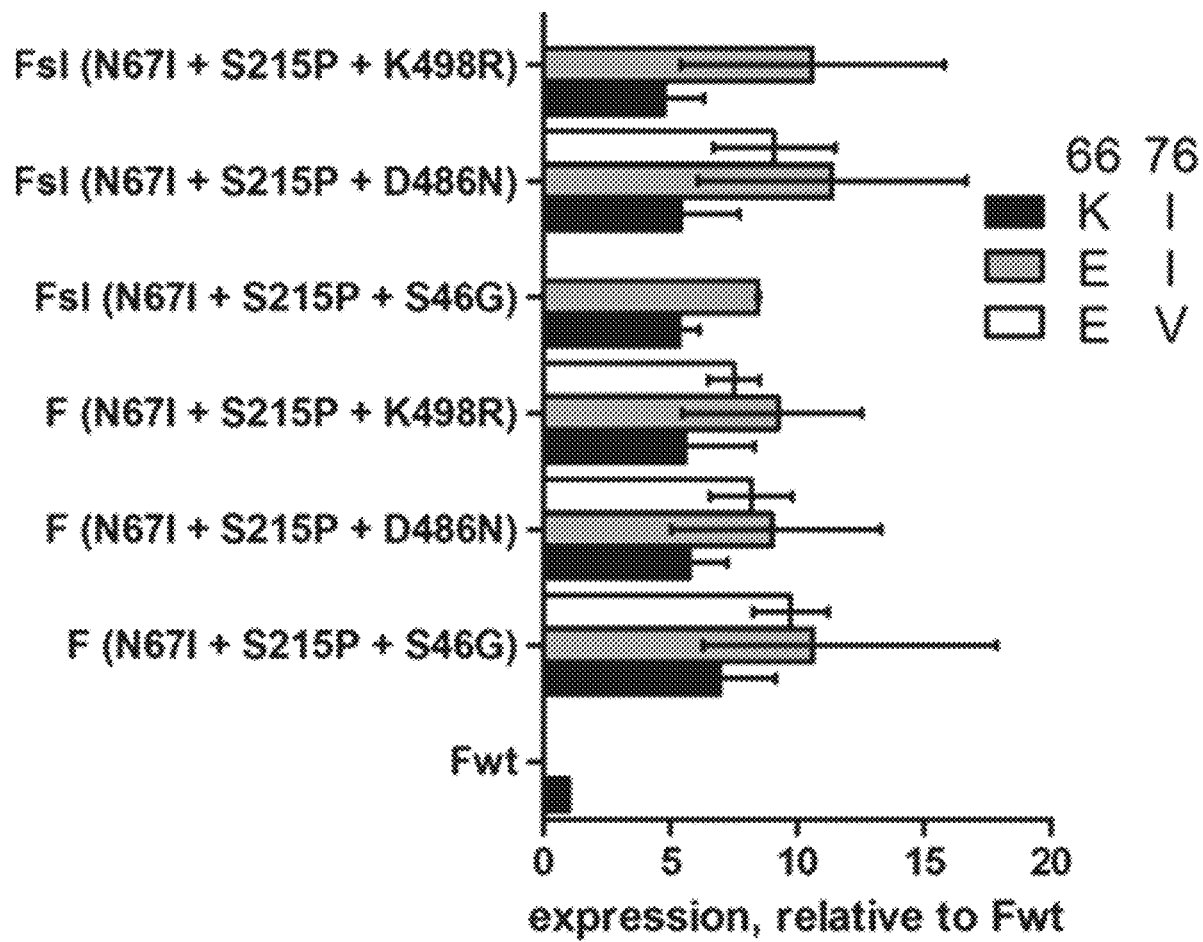
FIG. 4: Relative surface expression of F protein variants. Soluble versions with the transmembrane region and cytoplasmic region deleted (Fsl) and full length variants of F protein were expressed in HEK293T cells. The expression level of the soluble protein was measured in the culture supernatant by octet and the full length variants were tested by cell staining using anti-RSV F antibody (CR9503) and analyzed by Flow Cytometry. The Mean Fluorescent Intensity (MFI) values were calculated and normalized to MFI of control F wild type (Fwt)-transfected cell sample. The MFI of Fwt was set to 1. Bars represent mean values, error bars represent range of values.

The A2 strain that was used as a parental sequence for the previously described F protein variants (WO2014/174018 and WO2014/202570) is a cell line adapted laboratory strain which has accumulated two unique and rare mutations (i.e. of Lysine 66 and Isoleucine 76). In the present invention, these two residues were mutated to match the natural clinical isolates (K66E, I76V). The K66E and I76V mutations were included in selected protein designs. In comparison to variants with Lys66 and Ile76, variants with glutamate at 66 (K66E) have a tendency to express slightly higher. Addition of valine at residue 76 (a double substitution of K66E and I76V) does not influence expression level when compared to variants with K66E substitution alone (FIG. 4).

Figure 5A:
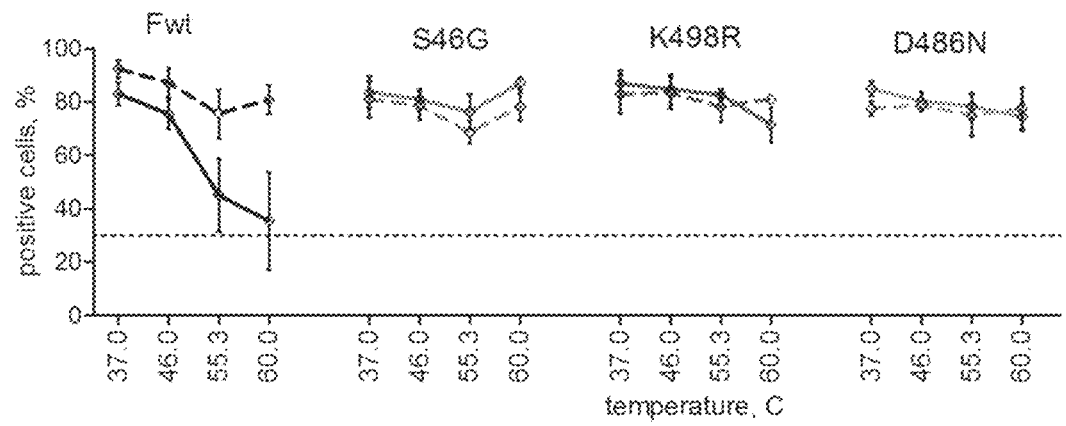
FIGS. 5A and 5B: Temperature stability of the F protein variants. Full length variants of F protein were expressed in HEK293T cells. After heat-shock, the cell were stained with anti-RSV F antibody (CR9501—solid lines and CR9503—dashed lines) and analyzed by Flow Cytometry. The percentage of cells positive for the staining was determined. Symbols represent mean values, error bars represent range of values.
Figure 5B:
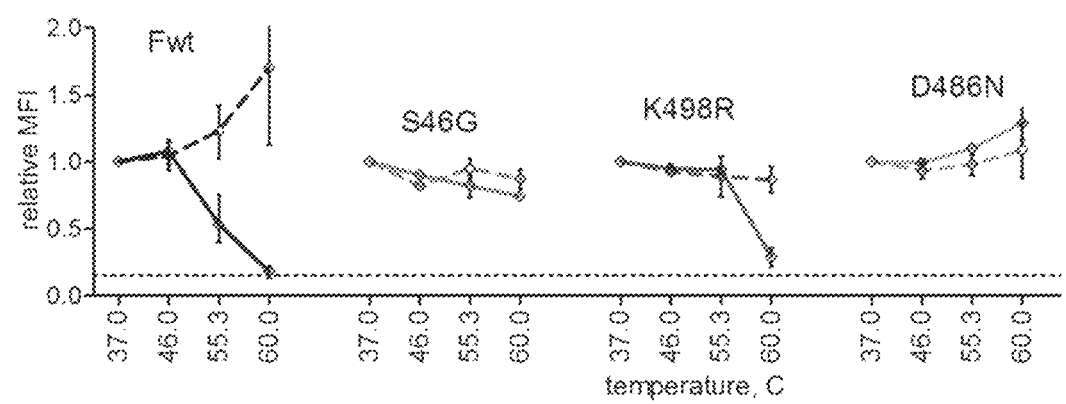

Stability of the Full Length F Protein Variants on the Cell Surface:

In ambient conditions on a short time scale, no significant difference in stability of pre-fusion conformation was observed between full length F variants with the different combinations of stabilizing mutations. An elevated temperature is known to serve as an efficient in vitro trigger for refolding of RSV F protein from pre-fusion to post-fusion conformation. Therefore, a heat-shock assay was established and used to assess stability of the membrane-bound full length proteins. Shortly, the HEK293T cells were transfected with the F protein constructs and used for the assay 48 hours after transfection. The cells were detached from cell culture dishes and the cell suspension was heat-treated at increasing temperatures for 10 minutes. After the heat-treatment, cells were stained with the anti-RSV F antibodies and analyzed by Flow Cytometry. The Flow Cytometry data was analyzed in two different ways. The percentage of the cells, positive for staining with the anti-F antibodies was analyzed, and also mean fluorescence intensity (MFI) of the positive cells was calculated (FIGS. 5A and 5B).

Both staining with CR9501 (antibody recognizing only pre-fusion F protein) and CR9503 (antibody recognizing both pre- and post-fusion F protein) were used in the Flow Cytometry assays. CR9503 antibody served as a positive control. In case when F protein loses pre-fusion conformation but still is on the surface of the cell, the protein is still detected with the CR9503 antibody. Loss of staining with both antibodies indicates that protein is not available on the cell surface for antibody binding, e.g. due to aggregation.

Full length proteins with three of more amino acid substitutions were tested in the assay and compared to the wild type RSV F. The expression of these variants was the highest and therefore these variants were preferred candidates. All of the proteins contained the N67I and S215P substitutions, and one or two extra stabilizing mutations were added.

The unmodified wild type protein had a rather stable staining with CR9503 antibody. The MFI of the CR9503 staining was elevated at higher temperatures however the spread of values was also very high. This indicated that no protein aggregation occurred after the heat-shock. Half of the pre-fusion conformation was lost after incubation of cells at approximately 55° C., after incubation of at 60° C. all pre-fusion conformation was lost as was demonstrated by decreased CR9501 binding to the wild type F samples after heat-shock at increasing temperatures.

Figure 6:
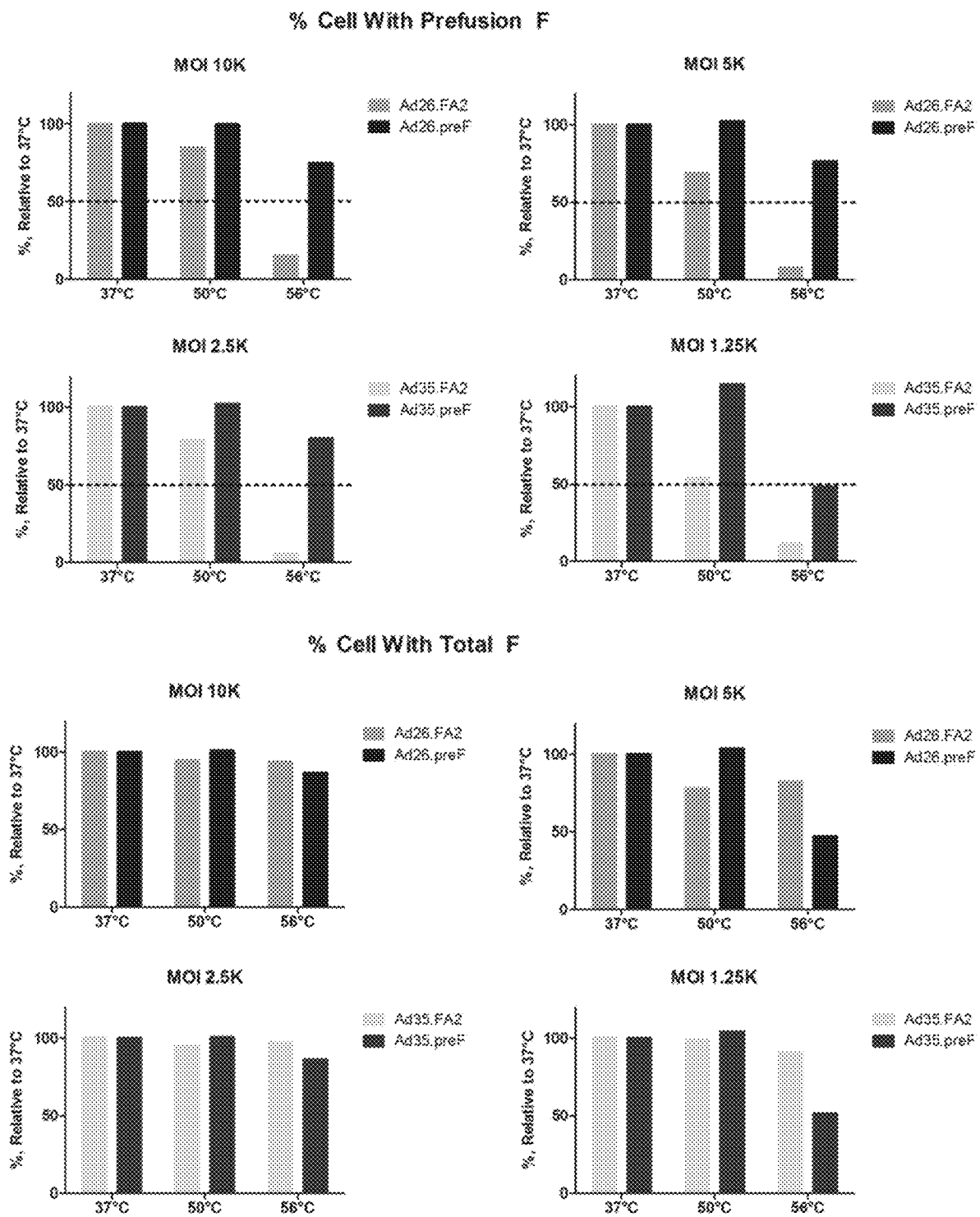
FIG. 6: Stability of the F proteins. PreF is more stable than FA2 protein in prefusion conformation on the cell surface in the heat-stress assay. A549 cells were infected with Ad26 and Ad35 comprising the insert FA2 (wt RSV F, grey bars) or prefusion F stabilized insert (preF2.2, black bars) at the indicated MOI. The cells were temperature treated at the indicated temperature for 15 minutes before staining. Top: percentage of cells presenting prefusion F on their surface (detected by CR9501 antibody); bottom: percentage of cells presenting any form of the F protein, prefusion and post fusion (detected by CR9503 antibody). The values were normalized to 37° C. samples. All bars represent a single measurement.
Figure 7:
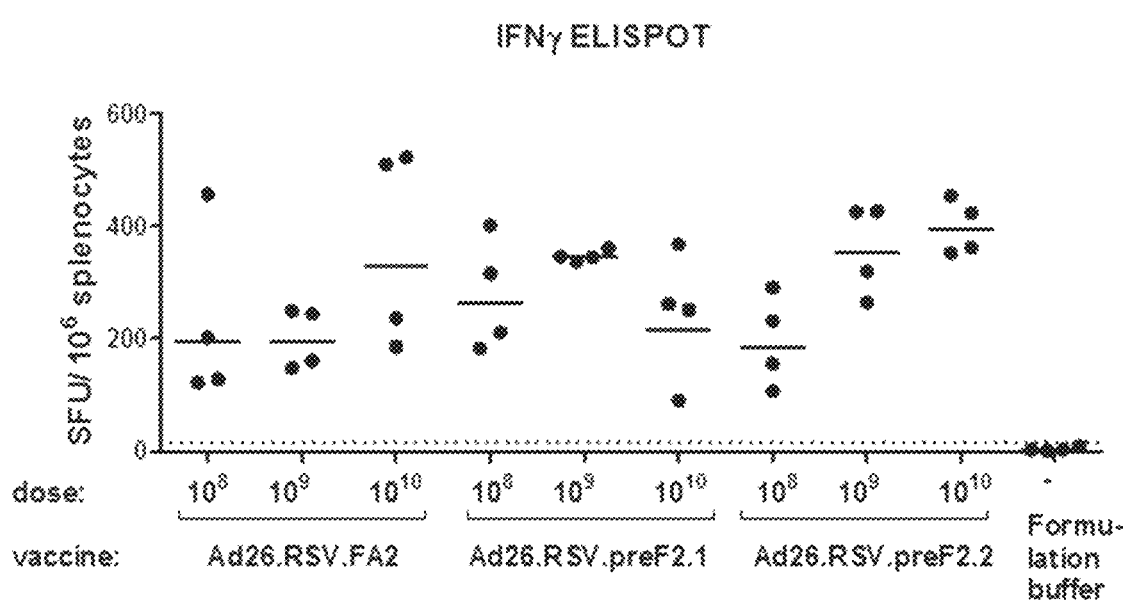
FIG. 7: Ad26.RSV.preF2.1 and F2.2 elicit a cellular immune response after single administration in mice. Horizontal bars depict the geometric mean of the response within a group. The background level is calculated as the 95% percentile of the spot forming units (SFU) observed in non-stimulated splenocytes, and is indicated with a dotted line.
Figure 8A:
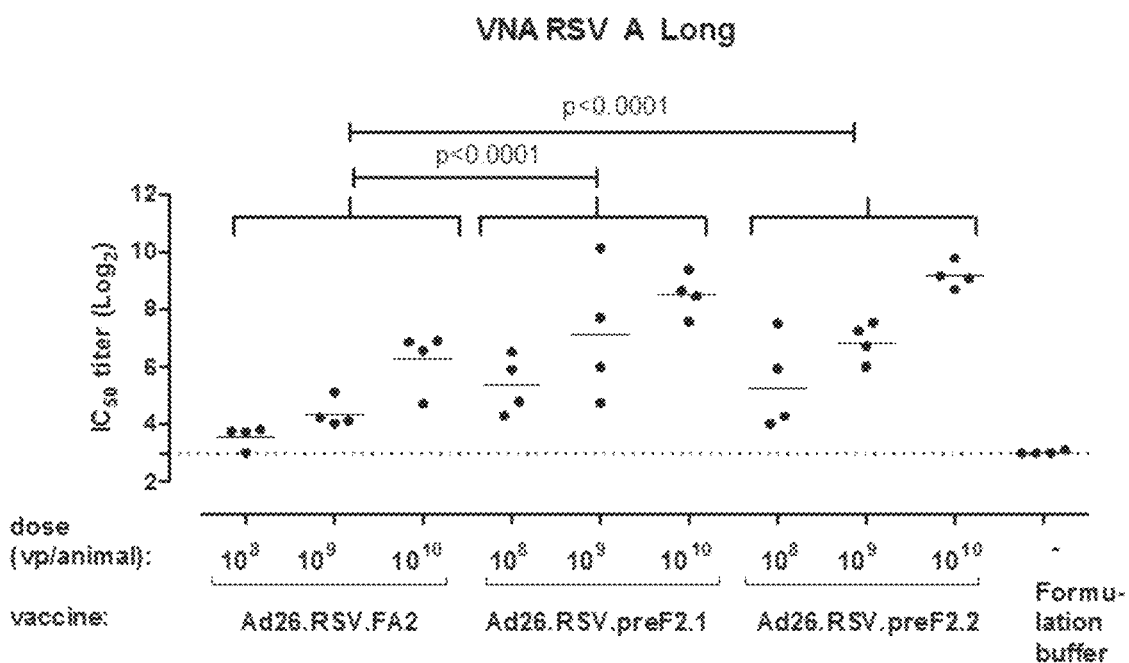
FIGS. 8A, 8B, and 8C: Ad26.RSV.preF2.1 and F2.2 induce increased virus neutralizing antibodies when compared to Ad26.RSV.FA2, after single immunization in mice. Balb/c mice (n=4 per group) were immunized with the indicated dose of 108 to 1010 viral particles (vp) Ad26.RSV.FA2 or Ad26.RSV.preF2.1 or Ad26.RSV.preF2.2, or with formulation buffer, and humoral immune responses were assayed in the serum isolated 8 weeks after immunization.
Figure 8B:
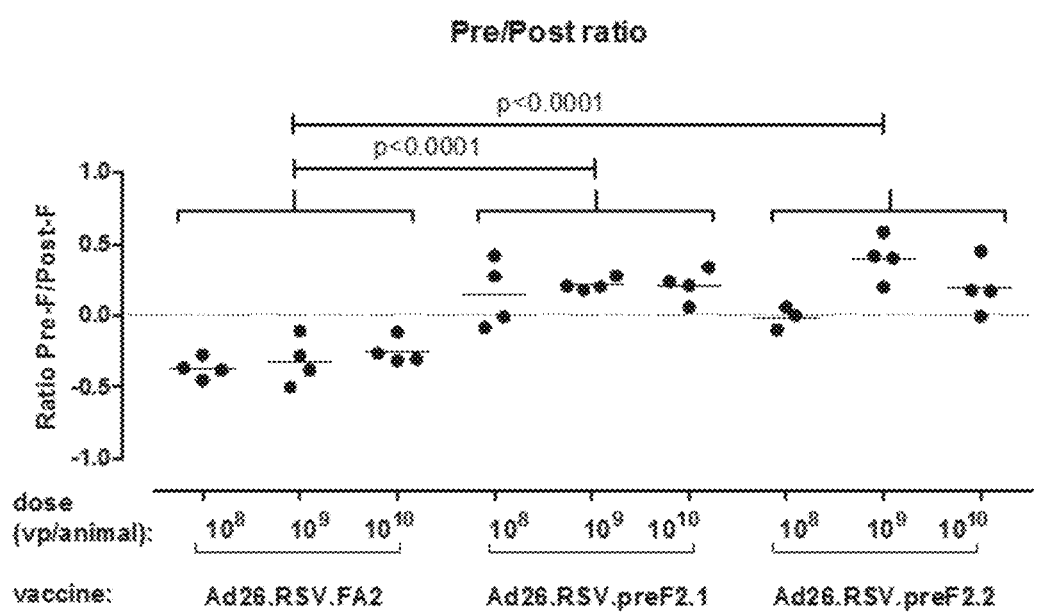
Figure 8C:
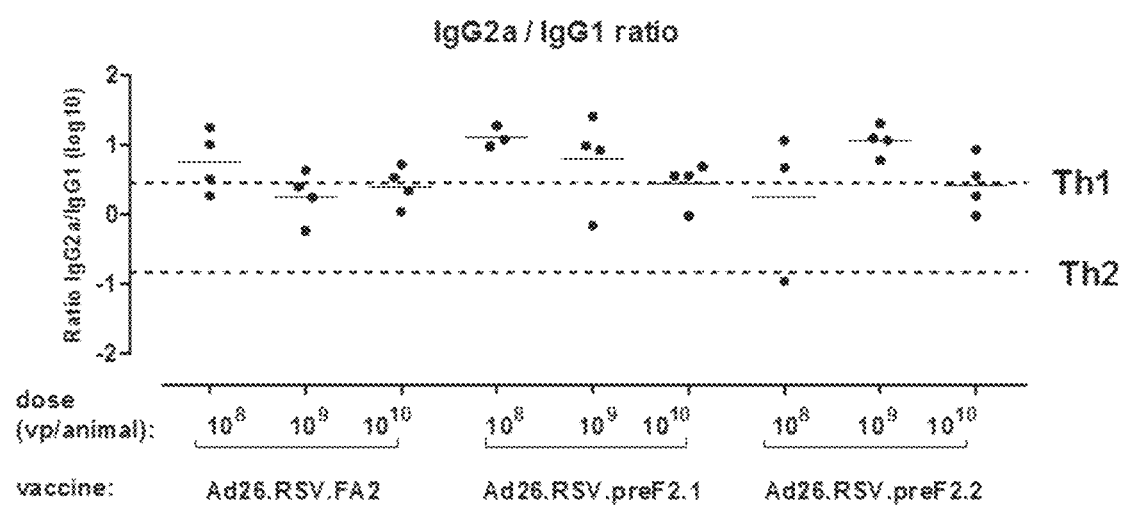
Figure 9:
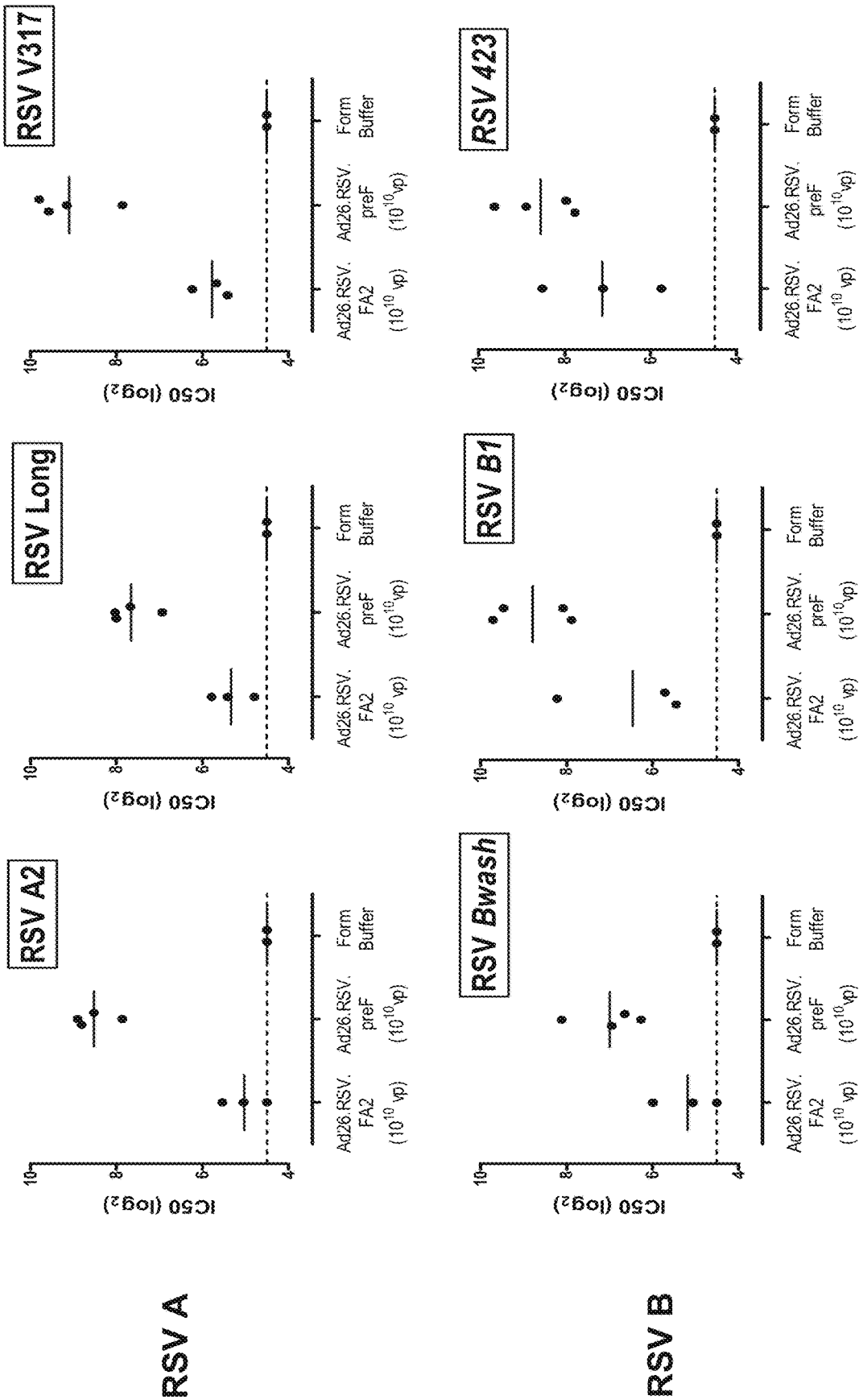
FIG. 9: Ad26.RSV.preF2.2 elicits antibody responses that neutralize a wide range of RSV isolates. Sera from Balb/c mice that were immunized with 1010 viral particles (vp)

All tested pre-fusion F protein variants were more stable than the wild type RSV F with majority of the CR9501 staining retaining also after treatment at higher temperatures (FIGS. 5A, 5B, and 6). Proteins with K498R amino acid substitution were less stable than the others. Addition of the K66E mutation further stabilized the proteins as also variants with K498R amino acid substitution became as stable as others and no loss of the pre-fusion conformation was observed at 60° C. Only selected combinations of the stabilizing mutations were tested with K66E and I76V combined. All four tested proteins were stable when percentage of positive cells was analyzed, however when MFI was analyzed variant with K498R showed clear decrease in CR9501 binding after treatment with 60° C., indicating that this variant is less stable when evaluated in the temperature stress assay.

In conclusion, a combination of three stabilizing mutations (including N67I and S215P) was considered sufficient for high expression level and stability. The S46G or D486N mutations was selected as a third stabilizing mutation because of their position in the protein structure. K66E and I76V were included in the as they did not have negative effect on the protein expression and stability but made the sequence closer to naturally occurring ones.

Thus, the pre-fusion RSV F protein with the mutations K66E, N67I, I76V, S215P and D486N (F2.2) (SEQ ID NO: 2) and the pre-fusion RSV F protein with the mutations K66E, N67I, I76V, S215P and S46G (F2.1) (SEQ ID NO: 1) were selected for the construction adenoviral vectors. These proteins were shown to be stable in the pre-fusion conformation in the temperature stability assay up to 60° C., and to be expressed in high levels.

Example 2. Preparation of Adenoviral Vectors

Cloning RSV F Gene into E1 Region of Ad35 and Ad26:

The nucleic acid sequences, coding for the pre-fusion F proteins of the invention were gene optimized for human expression and synthesized, by Geneart. A Kozak sequence (5' GCCACC 3' (SEQ ID NO: 5)) was included directly in front of the ATG start codon, and two stop codons (5' TGA TAA 3' (SEQ ID NO: 6)) were added at the end of the RSV.pre-F coding sequence. The RSV.pre-F genes were inserted in the pAdApt35BSU plasmid and in the pAdApt26 plasmid via HindIII and XbaI sites.

Cell Culture:

PER.C6 cells (Fallaux et al., 1998, *Hum Gene Ther* 9: 1909-1917) were maintained in Dulbecco's modified Eagle's medium (DMEM) with 10% fetal bovine serum (FBS), supplemented with 10 mM $MgCl_2$.

Adenovirus Generation, Infections and Passaging:

All adenoviruses were generated in PER.C6® cells by single homologous recombination and produced as previously described (for rAd35: Havenga et al., 2006, *J Gen. Virol.* 87: 2135-2143; for rAd26: Abbink et al., 2007, *J. Virol.* 81: 4654-4663). Briefly, PER.C6 cells were transfected with Ad vector plasmids, using Lipofectamine according to the instructions provided by the manufacturer (Life Technologies). For rescue of e.g. Ad35 vectors carrying the RSV.pre-F transgenes expression cassette, the pAdApt35BSU.RSV.pre-F plasmid and pWE/Ad35.pIX-rITR.dE3.5orf6 cosmid were used, whereas for Ad26 vectors carrying the RSV.pre-F transgene expression cassette, the pAdApt26.RSV.pre-F plasmid and pWE.Ad26.dE3.5orf6.cosmid were used. Cells were harvested one day after full CPE, freeze-thawed, centrifuged for 5 min at 3,000 rpm, and stored at −20° C. Next the viruses were plaque purified and amplified in PER.C6 cultured on a single well of a multiwell 24 tissue culture plate. Further amplification was carried out in PER.C6 cultured using a T25 tissue culture flask and a T175 tissue culture flask. Of the T175 crude lysate, 3 to 5 ml was used to inoculate 20×T175 triple-layer tissue culture flasks containing 70% confluent layers of PER.C6 cells. The virus was purified using a two-step CsCl purification method. Finally, the virus was stored in aliquots at −85° C.

Example 3. Induction of Immunity Against RSV F Using Recombinant Adenovirus Serotypes 26 and 35 Expressing Pre Fusion RSV F In Vivo The immunogenicity of Ad26.RSV.preF2.1 and Ad26.RSV.preF.2.2 was evaluated in mice, comparing cellular and humoral immune responses to responses induced by identical doses of Ad26.RSV.FA2 (i.e. expressing the wild type RSV F protein). Balb/c mice (n=4 per group) were immunized with the indicated dose of $10^8$ to $10^{10}$ viral particles (vp) Ad26.RSV.FA2 or Ad26.RSV.preF2.1 or Ad26.RSV.preF2.2, or with formulation buffer. At 8 weeks after prime, the number of RSV F A2 specific IFNγ spot forming units (SFU) per $10^6$ splenocytes was determined using ELISpot. It was shown that Ad26.RSV.preF2.1 and Ad26.RSV.preF.2.2 induced increased humoral immune responses in mice when compared to Ad26.RSV.FA2, with broad neutralizing capacity and maintained cellular responses. A single intramuscular immunization with Ad26.RSV.preF2.1 and Ad26.RSV.preF.2.2 elicited a cellular response (FIG. 7) which was characterized by induction of CD8+ T cells positive for IFNγ, IL2 and/or TNFα (data not shown).

The quantity and quality of the cellular responses were comparable between Ad26.RSV.preF2.1, Ad26.RSV.preF.2.2 and Ad26.RSV.FA2. In contrast, Ad26.RSV.preF2.1 and Ad26.RSV.preF.2.2 induced significantly higher RSV neutralizing antibody titers than Ad26.RSV.FA2. Closer analysis of the antibody responses demonstrated that Ad26.RSV.preF2.1 and Ad26.RSV.preF.2.2 induced higher levels of antibodies against pre-fusion F, while post-fusion F titers remained comparable to Ad26.RSV.FA2, resulting in significantly increased preF/postF antibody ratios. In addition, the IgG2a/IgG1 ratio of the antibody response remained unaltered, demonstrating a similar Th1 skewing of the humoral response as previously demonstrated for Ad26.RSV.FA2 (FIGS. 8A, 8B, and 8C).

For Ad26.RSV.preF2.2 it was furthermore demonstrated that the antibodies elicited were capable of neutralizing various RSV A and B strains, laboratory strains as well as clinical isolates, similar as observed for Ad26.RSV.FA2 (FIG. 9).

Subsequently, the efficacy and immunogenicity of Ad26.RSV.preF2.2 and Ad35.RSV.preF2.2 vector constructs was evaluated in the cotton rat model. These animals are permissive to replication of human RSV, with peak RSV titers in the lungs at days 4 and 5. Control groups in the experiments included groups intranasally infected with a low dose RSV A2, thereby mimicking natural exposure, as well as groups immunized with FI-RSV, using the original lot 100 that induced enhanced respiratory disease (ERD) in clinical studies in the dilution that was shown to induce ERD in cotton rats.

Figure 10A:
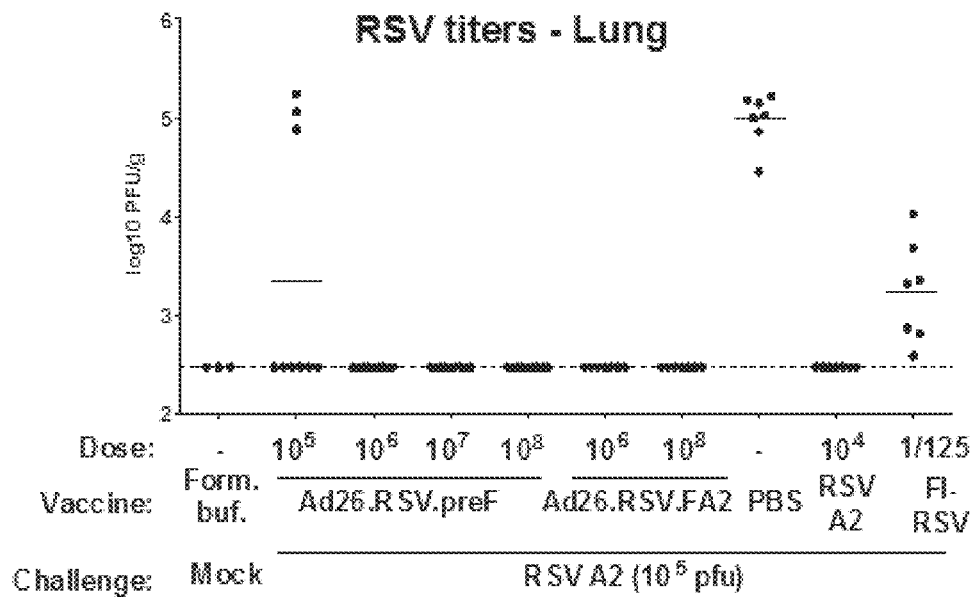
Figure 10B:
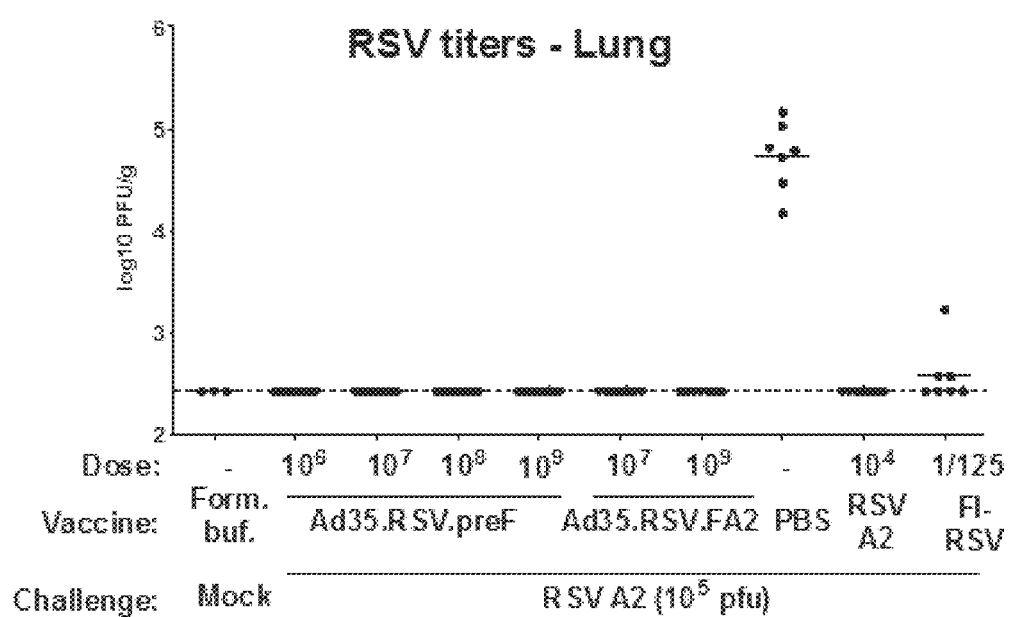
Figure 10C:
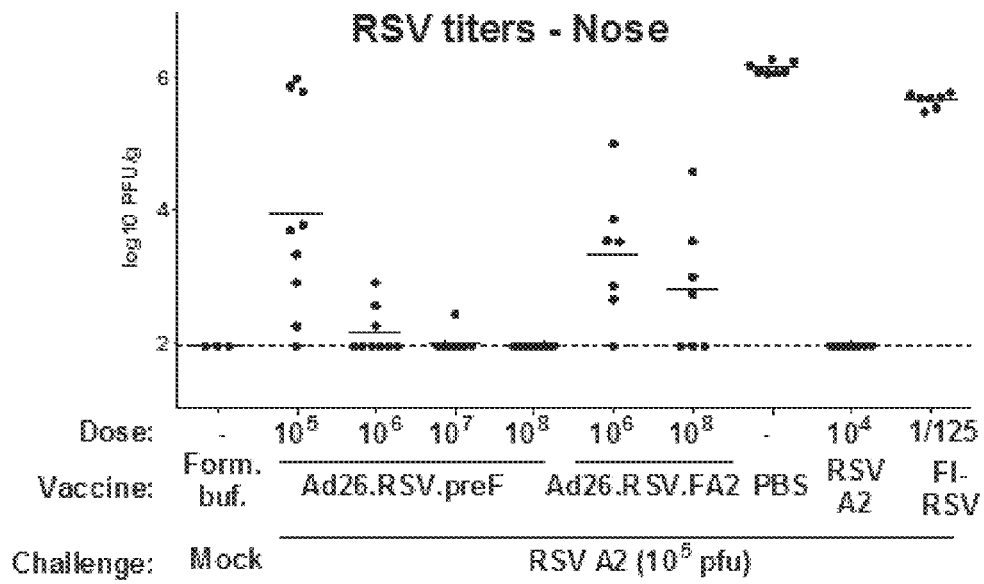
Figure 10D:
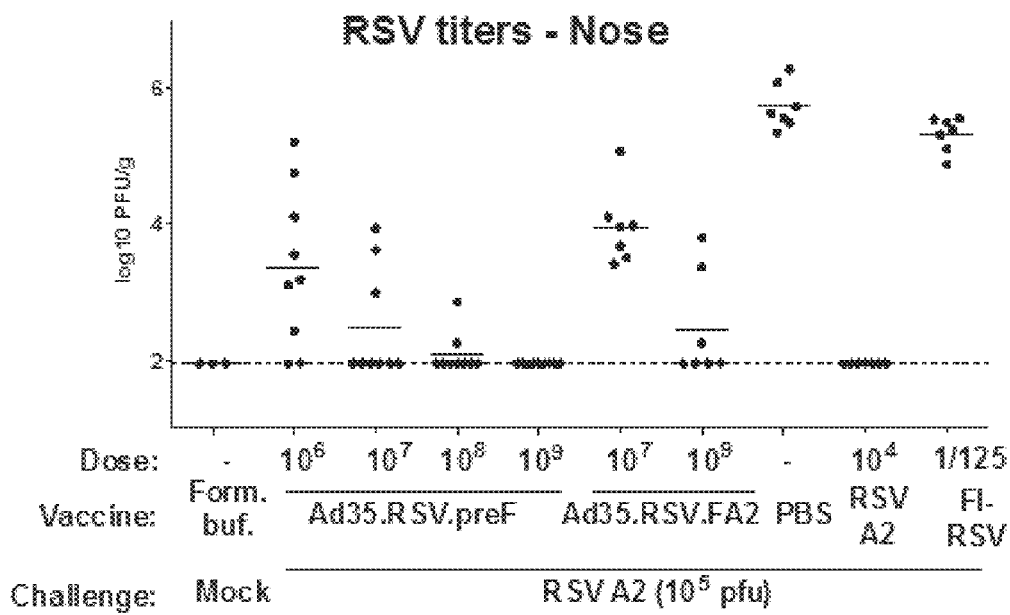
Figure 10E:
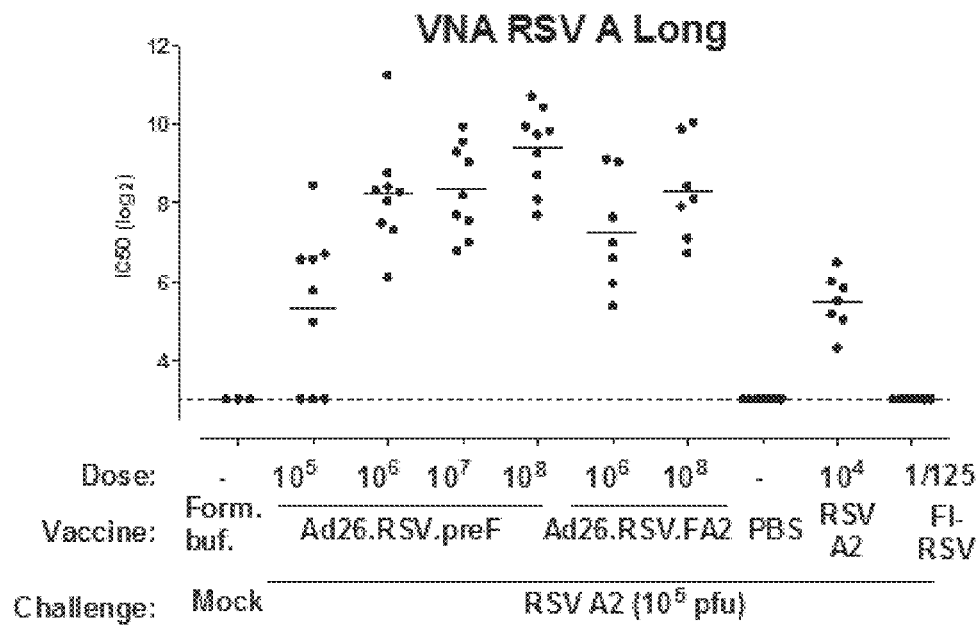
Figure 10F:
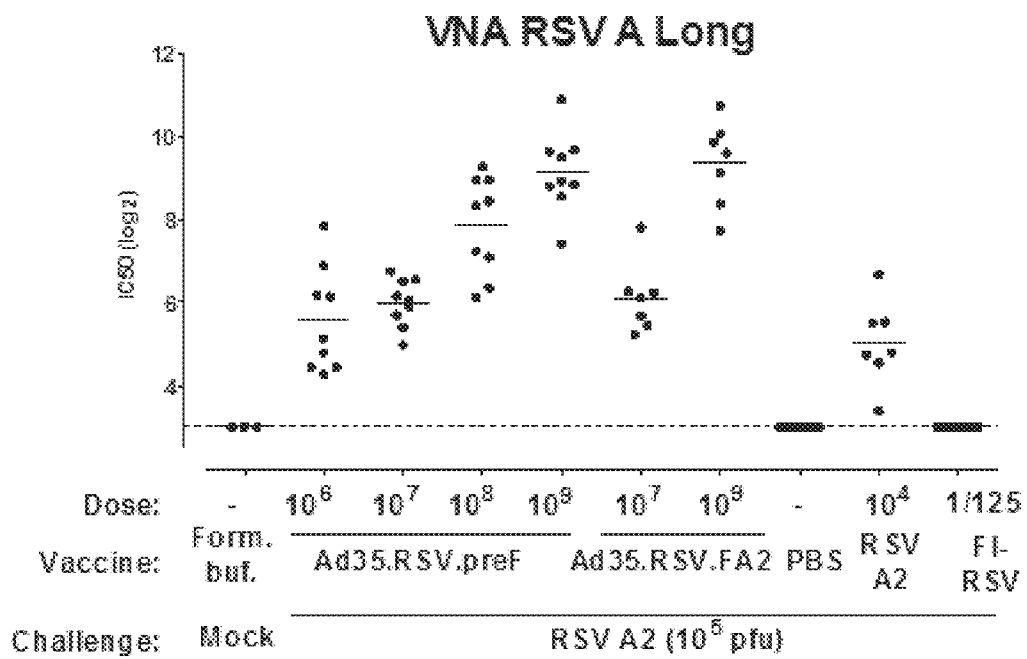

Single intramuscular immunization of animals with Ad26.RSV.preF2.2 in doses ranging from $10^5$ to $10^8$ vp/animal, or Ad35.RSV.preF2.2 in doses ranging from $10^6$ to $10^9$ vp/animal resulted in complete protection of the lungs from infection with the vaccine homologous RSV A2 strain, except for 3 animals immunized with $10^5$ vp Ad26.RSV.preF2.2 (FIGS. 10A and 10B). Dose dependent protection of RSV replication in the nose was observed for both vectors. This ranged from full protection at $10^8$ vp/animal, to partial protection at $10^5$ vp for Ad26.RSV.preF2.2, whereas for Ad35.RSV.preF2.2, noses of animals immunized with $10^9$ vp were fully protected from RSV A2, and $10^6$ vp resulted in partial protection (FIGS. 10C and 10D) Noses of animals immunized with Ad26.RSV.preF2.2 and Ad35.RSV.preF2.2 were better protected from RSV A2 infection than when immunized with their respective wild type F counterparts Ad26.RSV.FA2 and Ad35.RSV.FA2, when analyzed across dose (p=0.0003, and p=0.0001). Protection from RSV infection was accompanied by dose-dependent induction of virus neutralization titers against RSV A Long, already elicited by the lowest doses of Ad26.RSV.preF2.2 or Ad35.RSV.preF2.2 applied (FIGS. 10E and 10F). Across dose statistical comparisons of VNA A Long titers revealed that Ad26.RSV.preF2.2 is more immunogenic than Ad26.RSV.FA2 (p=0.0414), whereas elicitation of VNA titers was not significantly different between Ad35.RSV.preF2.2 and Ad35.RSV.FA2.

It was further demonstrated that Ad26.RSV.preF and Ad35.RSV.preF do not induce histopathological signs of Enhanced Respiratory Disease (ERD) after RSV A2 challenge, at any of the concentrations tested. The cotton rat is the most used and best studied model to monitor ERD. In this animal model, vaccination with FI-RSV consistently induces ERD after RSV challenge, which is visible by histopathological analysis of sections of the infected lungs for parameters as alveolitits, consisting primarily of neutrophil infiltrates, and peribronchiolitis, consisting primarily of lymphocyte infiltrates. In cotton rats, FI-RSV-induced scores for these parameters can be observed from day 1 after RSV infection, and peak at 4 to 5 days after RSV challenge.

ERD was analyzed 5 days after challenge with RSV A2 by scoring 4 parameters of pulmonary inflammatory changes (peribronchiolitis, perivasculitis, interstitial pneumonia, alveolitis). Immunization with FI-RSV resulted in enhanced scores for most histopathological markers, which was especially apparent for alveolitis (FIG. 11), the marker that was previously shown to be the most discriminating marker for ERD. No increases in alveolitis or any other ERD histopathological marker was observed in animals immunized by either Ad26.RSV.preF2.2 or Ad35.RSV.preF2.2 in a prime-only regimen after RSV challenge, even at low vaccine doses that may induce low affinity and/or low levels of antibodies (FIG. 11). This is confirming our previous results with Ad26.RSV.FA2 and Ad35.RSV.FA2 vectors.

According to the invention, it has thus been shown that Ad26.RSV.preF and Ad35.RSV.preF are potent adenoviral vectors expressing RSV F A2 which is stabilized in the pre-fusion conformation. These vectors induce strong humoral and cellular immune responses. The immune response elicited is protective against RSV A2 challenge and provides a wide range of virus neutralization in vitro against clinical and laboratory isolates of RSV. No ERD induction was observed in cotton rats after RSV exposure of vaccinated animals and therefore confirms the data generated with Ad26 and Ad35 encoding for the wild type RSV F A2 antigen. Neither mice nor cotton rats showed overt signs of reactogenicity after injection of either Ad26.RSV.preF or Ad35.RSV.preF.

TABLE 1

Amino acid sequences of the RSV pre-fusion F
proteins encoded by the nucleic acid molecules of
the invention (mutations are underlined)

SEQ ID NO: 1: RSV preF2.1 amino acid sequence:
MELLILKANAITTILTAVTFCFASGQNITEEFYQSTCSAVSKGYL<u>G</u>ALRT GWYTSVITIELSNIK<u>EI</u>KCNGTDAK<u>V</u>KLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSI<u>PN</u>IETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPSDEFDASISQVNEKIN

QSLAFIRKSDELLHNVNAVKSTTNIMITTIIIVIIVILLSLIAVGLLLYC

KARSTPVTLSKDQLSGINNIAFSN

SEQ ID NO: 2: RSV preF2.2 amino acid sequence:
MELLILKANAITTILTAVTFCFASGQNITEEFYQSTCSAVSKGYLSALRT GWYTSVITIELSNIK<u>EI</u>KCNGTDAK<u>V</u>KLIKQELDKYKNAVTELQLLMQST

PATNNRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSI<u>PN</u>IETVIEFQQKNNRLLEITREFSVNAGVTTPVSTY

MLTNSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTMNSLTLPSEVNLCNVDIFNPKYDCKIMTSKT

DVSSSVITSLGAIVSCYGKTKCTASNKNRGIIKTFSNGCDYVSNKGVDTV

SVGNTLYYVNKQEGKSLYVKGEPIINFYDPLVFPS<u>NE</u>FDASISQVNEKIN

QSLAFIRKSDELLHNVNAVKSTTNIMITTIIIVIIVILLSLIAVGLLLYC

KARSTPVTLSKDQLSGINNIAFSN

TABLE 2

Nucleotide sequence of preferred nucleic acid molcules of the invention

SEQ ID NO: 3: codon optimized nucleic acid encoding the RSV F pre-F2.1 pre-fusion protein PreF2.1
ATGGAGCTGCTGATCCTGAAGGCCAACGCCATCACCACCATCCTGACCGC
CGTGACCTTCTGCTTCGCCAGCGGCCAGAACATCACCGAGGAGTTCTACC
AGAGCACCTGCAGCGCCGTGAGCAAGGGCTACCTGGGCGCCCTGAGAACC
GGCTGGTACACCAGCGTGATCACCATCGAGCTGAGCAACATCAAGGAGAT
CAAGTGCAACGGCACCGACGCCAAGGTGAAGCTGATCAAGCAGGAGCTGG
ACAAGTACAAGAACGCCGTGACCGAGCTGCAGCTGCTGATGCAGAGCACC
CCCGCCACCAACAACAGAGCCAGAAGAGAGCTGCCCAGATTCATGAACTA
CACCCTGAACAACGCCAAGAAGACCAACGTGACCCTGAGCAAGAAGAGAA
AGAGAAGATTCCTGGGCTTCCTGCTGGGCGTGGGCAGCGCCATCGCCAGC
GGCGTGGCCGTGAGCAAGGTGCTGCACCTGGAGGGCGAGGTGAACAAGAT
CAAGAGCGCCCTGCTGAGCACCAACAAGGCCGTGGTGAGCCTGAGCAACG
GCGTGAGCGTGCTGACCAGCAAGGTGCTGGACCTGAAGAACTACATCGAC
AAGCAGCTGCTGCCCATCGTGAACAAGCAGAGCTGCAGCATCCCCAACAT
CGAGACCGTGATCGAGTTCCAGCAGAAGAACAACAGACTGCTGGAGATCA
CCAGAGAGTTCAGCGTGAACGCCGGCGTGACCACCCCCGTGAGCACCTAC
ATGCTGACCAACAGCGAGCTGCTGAGCCTGATCAACGACATGCCCATCAC
CAACGACCAGAAGAAGCTGATGAGCAACAACGTGCAGATCGTGAGACAGC
AGAGCTACAGCATCATGAGCATCATCAAGGAGGAGGTGCTGGCCTACGTG
GTGCAGCTGCCCCTGTACGGCGTGATCGACACCCCCTGCTGGAAGCTGCA
CACCAGCCCCCTGTGCACCACCAACACCAAGGAGGGCAGCAACATCTGCC
TGACCAGAACCGACAGAGGCTGGTACTGCGACAACGCCGGCAGCGTGAGC
TTCTTCCCCCAGGCCGAGACCTGCAAGGTGCAGAGCAACAGAGTGTTCTG
CGACACCATGAACAGCCTGACCCTGCCCAGCGAGGTGAACCTGTGCAACG
TGGACATCTTCAACCCCAAGTACGACTGCAAGATCATGACCAGCAAGACC
GACGTGAGCAGCAGCGTGATCACCAGCCTGGGCGCCATCGTGAGCTGCTA
CGGCAAGACCAAGTGCACCGCCAGCAACAAGAACAGAGGCATCATCAAGA
CCTTCAGCAACGGCTGCGACTACGTGAGCAACAAGGGCGTGGACACCGTG
AGCGTGGGCAACACCCTGTACTACGTGAACAAGCAGGAGGGCAAGAGCCT
GTACGTGAAGGGCGAGCCCATCATCAACTTCTACGACCCCCTGGTGTTCC
CCAGCGACGAGTTCGACGCCAGCATCAGCCAGGTGAACGAGAAGATCAAC
CAGAGCCTGGCCTTCATCAGAAAGAGCGACGAGCTGCTGCACAACGTGAA
CGCCGTGAAGAGCACCACCAACATCATGATCACCACCATCATCATCGTGA
TCATCGTGATCCTGCTGAGCCTGATCGCCGTGGGCCTGCTGCTGTACTGC
AAGGCCAGAAGCACCCCCGTGACCCTGAGCAAGGACCAGCTGAGCGGCAT
CAACAACATCGCCTTCAGCAACTGA SEQ ID NO: 4: codon optimized nucleic acid encoding the RSV F pre-F2.2 pre-fusion protein PreF2.2
ATGGAGCTGCTGATCCTGAAGGCCAACGCCATCACCACCATCCTGACCGC
CGTGACCTTCTGCTTCGCCAGCGGCCAGAACATCACCGAGGAGTTCTACC
AGAGCACCTGCAGCGCCGTGAGCAAGGGCTACCTGAGCGCCCTGAGAACC
GGCTGGTACACCAGCGTGATCACCATCGAGCTGAGCAACATCAAGGAGAT
CAAGTGCAACGGCACCGACGCCAAGGTGAAGCTGATCAAGCAGGAGCTGG
ACAAGTACAAGAACGCCGTGACCGAGCTGCAGCTGCTGATGCAGAGCACC
CCCGCCACCAACAACAGAGCCAGAAGAGAGCTGCCCAGATTCATGAACTA
CACCCTGAACAACGCCAAGAAGACCAACGTGACCCTGAGCAAGAAGAGAA
AGAGAAGATTCCTGGGCTTCCTGCTGGGCGTGGGCAGCGCCATCGCCAGC
GGCGTGGCCGTGAGCAAGGTGCTGCACCTGGAGGGCGAGGTGAACAAGAT
CAAGAGCGCCCTGCTGAGCACCAACAAGGCCGTGGTGAGCCTGAGCAACG
GCGTGAGCGTGCTGACCAGCAAGGTGCTGGACCTGAAGAACTACATCGAC
AAGCAGCTGCTGCCCATCGTGAACAAGCAGAGCTGCAGCATCCCCAACAT
CGAGACCGTGATCGAGTTCCAGCAGAAGAACAACAGACTGCTGGAGATCA
CCAGAGAGTTCAGCGTGAACGCCGGCGTGACCACCCCCGTGAGCACCTAC
ATGCTGACCAACAGCGAGCTGCTGAGCCTGATCAACGACATGCCCATCAC
CAACGACCAGAAGAAGCTGATGAGCAACAACGTGCAGATCGTGAGACAGC
AGAGCTACAGCATCATGAGCATCATCAAGGAGGAGGTGCTGGCCTACGTG
GTGCAGCTGCCCCTGTACGGCGTGATCGACACCCCCTGCTGGAAGCTGCA
CACCAGCCCCCTGTGCACCACCAACACCAAGGAGGGCAGCAACATCTGCC
TGACCAGAACCGACAGAGGCTGGTACTGCGACAACGCCGGCAGCGTGAGC
TTCTTCCCCCAGGCCGAGACCTGCAAGGTGCAGAGCAACAGAGTGTTCTG
CGACACCATGAACAGCCTGACCCTGCCCAGCGAGGTGAACCTGTGCAACG
TGGACATCTTCAACCCCAAGTACGACTGCAAGATCATGACCAGCAAGACC
GACGTGAGCAGCAGCGTGATCACCAGCCTGGGCGCCATCGTGAGCTGCTA
CGGCAAGACCAAGTGCACCGCCAGCAACAAGAACAGAGGCATCATCAAGA
CCTTCAGCAACGGCTGCGACTACGTGAGCAACAAGGGCGTGGACACCGTG
AGCGTGGGCAACACCCTGTACTACGTGAACAAGCAGGAGGGCAAGAGCCT
GTACGTGAAGGGCGAGCCCATCATCAACTTCTACGACCCCCTGGTGTTCC
CCAGCAACGAGTTCGACGCCAGCATCAGCCAGGTGAACGAGAAGATCAAC
CAGAGCCTGGCCTTCATCAGAAAGAGCGACGAGCTGCTGCACAACGTGAA
CGCCGTGAAGAGCACCACCAACATCATGATCACCACCATCATCATCGTGA
TCATCGTGATCCTGCTGAGCCTGATCGCCGTGGGCCTGCTGCTGTACTGC
AAGGCCAGAAGCACCCCCGTGACCCTGAGCAAGGACCAGCTGAGCGGCAT
CAACAACATCGCCTTCAGCAACTGA

What is claimed is:

1. A vaccine comprising a polynucleotide sequence that encodes a respiratory syncytial virus (RSV) pre-fusion F protein having the amino acid sequence of SEQ ID NO: 1 or SEQ ID NO: 2.

* * * * *